US011725187B2

(12) United States Patent
Sauvageau et al.

(10) Patent No.: US 11,725,187 B2
(45) Date of Patent: Aug. 15, 2023

(54) SELECTION OF HUMAN HEMATOPOETIC STEM CELLS USING EPCR

(71) Applicant: UNIVERSITE DE MONTREAL, Montréal (CA)

(72) Inventors: Guy Sauvageau, Montréal (CA); Iman Fares, Boston, MA (US); Jalila Chagraoui, Montreal (CA)

(73) Assignee: UNIVERSITE DE MONTREAL, Montreal (CA)

( * ) Notice: Subject to any disclaimer, the term of this patent is extended or adjusted under 35 U.S.C. 154(b) by 582 days.

(21) Appl. No.: 16/099,551

(22) PCT Filed: May 31, 2017

(86) PCT No.: PCT/CA2017/050661
§ 371 (c)(1),
(2) Date: Nov. 7, 2018

(87) PCT Pub. No.: WO2017/205977
PCT Pub. Date: Dec. 7, 2017

(65) Prior Publication Data
US 2019/0085291 A1    Mar. 21, 2019

Related U.S. Application Data

(60) Provisional application No. 62/344,011, filed on Jun. 1, 2016.

(51) Int. Cl.
*C12N 5/0789* (2010.01)
*A61K 35/28* (2015.01)
*A61K 35/14* (2015.01)
*C07K 14/74* (2006.01)
*C12M 3/06* (2006.01)
*G01N 33/569* (2006.01)
*C12N 15/113* (2010.01)
*A61K 35/51* (2015.01)

(52) U.S. Cl.
CPC ............ *C12N 5/0647* (2013.01); *A61K 35/14* (2013.01); *A61K 35/28* (2013.01); *C07K 14/70539* (2013.01); *C12M 3/06* (2013.01); *C12N 15/1138* (2013.01); *G01N 33/56966* (2013.01); *A61K 35/51* (2013.01); *C12N 2501/50* (2013.01); *C12N 2501/599* (2013.01); *G01N 33/569* (2013.01)

(58) Field of Classification Search
None
See application file for complete search history.

(56) References Cited

U.S. PATENT DOCUMENTS

| | | | |
|---|---|---|---|
| 2008/0188500 A1 | 8/2008 | Arvanitis | |
| 2008/0207632 A1 | 8/2008 | Bearss | |
| 2009/0029982 A1 | 1/2009 | Bearss | |
| 2009/0062318 A1 | 3/2009 | Gangjee | |
| 2010/0210639 A1 | 8/2010 | Collins | |
| 2011/0212929 A1 | 9/2011 | Hurley | |
| 2012/0121552 A1 | 5/2012 | Balazs et al. | |
| 2015/0246934 A1 | 9/2015 | Bensen | |
| 2016/0244768 A1* | 8/2016 | Tachas | A61K 38/193 |
| 2017/0173083 A1* | 6/2017 | Federation | A61K 35/28 |
| 2020/0248143 A1* | 8/2020 | Rossi | A61P 3/10 |

FOREIGN PATENT DOCUMENTS

| | | |
|---|---|---|
| WO | 2005042731 | 5/2005 |
| WO | WO2005042731 | * 12/2005 |
| WO | 2011056739 | 5/2011 |
| WO | 2015161373 | 10/2015 |
| WO | 2016176772 | 11/2016 |

OTHER PUBLICATIONS

Fares et al ., Science, 2014, v.345, pp. 1509-1512.*
Alejandro Balazs et al. "Endothelial protein C receptor (CD201) explicitly identifies hematopoietic stem cells in murine bone marrow", Blood, vol. 107, No. 6, Mar. 15, 2006, pp. 2317-2321.
Iman Fares et al., "EPCR expression marks UM171-expanded CD34 1 cord blood stem cells" Blood, vol. 129, No. 25, Sep. 19, 2014, pp. 3344 3351.
Iman Fares et al. "Cord blood expansion. Pyrimidoindole derivatives are agonists of human hematopoietic stem cell self-renewal", Science, vol. 345, No. 6203, Sep. 19, 2014, pp. 1509-1512.
Zhang Yu et al., "Novel chemical attempts at ex vivo hematopoietic stem cell expansion", international Journal of Hematology, Elsevier Science Publishers, NL, vol. 103, No. 5, Feb. 24, 2016, pp. 519-529.
A. E. Boitano et al., "aryl Hydrocarbon Receptor Antagonists Promote the Expansion of Human Hematoppoietic Stem Cells", Science, vol. 329, No. 5997, Sep. 10, 2010, pp. 1345-1348.
Boirano et al. "Aryl hydocarbon receptor antagonists promote the expansion of human hematopoietic stem cells" Science, Sep. 2010, vol. 329(5997), pp. 1345-1348.
Bundy, Gordon L. et al. "Synthesis of 2, 4-di-1-pyrrolidinyl-9H-pyrimido[4,5-b]indoles, including antiasthma clinical candidate PNU-142731A", Organic Process Research and Development, 2001.
Showalter, H.D. Hollis et al, "Tyrosine Kinase inhibitors. 16. 6, 5, 6-Tricydic benzothieno[3,2-d]pyrimidines and pyrimido]5,4,-b]- and -[4,5-b]indoles as potent inhibitors of the epidermal growth factor receptor tyrosine kinase", Journal of Medicinal Chemistry, 2009.
Venugopalan, et al. "Synthesis of 6,7-dimethyoxypyrimidol[4,5-b]-indoles as potential antihypertensive agents", Journal of Heterocyclic Chemistry, 1988.
Kittlemann, Matthias et al. "Microbial hydroxylation and simultaneous formation of the 4"-O-methylglucoside of the tyrosine-kinase inhibitor CGP 62706", Chimia, 1999.

* cited by examiner

*Primary Examiner* — Michail A Belyavskyi
(74) *Attorney, Agent, or Firm* — Norton Rose Fulbright Canada LLP

(57) ABSTRACT

It is provided a method of expanding ex vivo hematopoietic stem cells (HSC), the method comprising selecting a population of Endothelial Protein C Receptor (EPCR)+ HSC, culturing the selected HSC thereby expanding said EPCR+ HSC and the use of the expanded EPCR+ HSC for stem cells transplantation.

13 Claims, 35 Drawing Sheets

Specification includes a Sequence Listing.

| Sorted population (% at d7 prior to sorting) | Cell dose at d7 | %Avg. Hu-CD45 ± STD (wk24) | (E/T) | Frequency of LT-HSC | | Number (population %) of LT-HSC at d7 per 10³ CD34⁺CD45RA⁻ starting cell |
|---|---|---|---|---|---|---|
| | | | | Estimate | (95% CI) | |
| Total (100%) | 75,000 | 56.7±21 | (5/5) | 1:828 | (1,973;347) | 30.2 (100%) |
| | 25,000 | 6.2±8.1 | (4/4) | | | |
| | 8,333 | 3.7±4 | (5/5) | | | |
| | 2,778 | 1.7±2.5 | (5/5) | | | |
| | 926 | 0.1±0.2 | (3/5) | | | |
| EPCR⁺ (6%) | 4,500 | 54.1±18 | (5/5) | 1:68 | (155;30) | 22 (73%) |
| | 1,500 | 33±22.7 | (5/5) | | | |
| | 500 | 14.2±13.2 | (5/5) | | | |
| | 167 | 0.3±0.1 | (5/5) | | | |
| | 56 | 0.1±0.1 | (2/5) | | | |
| EPCRlow (84%) | 62,775 | 3.4±6.4 | (5/5) | 1:2,016 | (4,406;923) | 10.4 (34%) |
| | 20,925 | 0.6±0.1 | (5/5) | | | |
| | 6,975 | 0.4±0.2 | (5/5) | | | |
| | 2,325 | 0.1±0.1 | (4/5) | | | |
| | 775 | 0.1±0.0 | (0/4) | | | |
| EPCR⁻ (10%) | 7,575 | 0.1±0.1 | (3/5) | 1:4,240 | (8,824;2,037) | 0.6 (2%) |
| | 2,525 | 0.2±0.0 | (5/5) | | | |
| | 842 | 0.1±0.0 | (4/5) | | | |
| | 281 | 0.0±0.0 | (1/5) | | | |

FIG. 6A

SEQUENCE LISTING

<160> NUMBER OF SEQ ID NOS: 4

<210> SEQ ID NO 1
<211> LENGTH: 47
<212> TYPE: DNA
<213> ORGANISM: Artificial Sequence
<220> FEATURE:
<223> OTHER INFORMATION: miRE-Xho-fw-long

<400> SEQUENCE: 1
tgtgtgtgtg tgaactcgag aaggtatatt gctgttgaca gtgagcg        47

<210> SEQ ID NO 2
<211> LENGTH: 48
<212> TYPE: DNA
<213> ORGANISM: Artificial Sequence
<220> FEATURE:
<223> OTHER INFORMATION: miRE-EcoRI-rev-long

<400> SEQUENCE: 2
tctctctctc tctcgaattc tagccccttg aagtccgagg cagtaggc       48

<210> SEQ ID NO 3
<211> LENGTH: 75
<212> TYPE: DNA
<213> ORGANISM: Artificial Sequence
<220> FEATURE:
<223> OTHER INFORMATION: PROCR.1364 (shEPCR#1)

<400> SEQUENCE: 3
tgctgttgac agtgagcgat ggtggaaatg taaaatccaa tagtgaagcc acagatgtat    60
tggattttac atttc                                                    75

<210> SEQ ID NO 4
<211> LENGTH: 91
<212> TYPE: DNA
<213> ORGANISM: Artificial Sequence
<220> FEATURE:
<223> OTHER INFORMATION: PROCR.1240 (shEPCR#2)

<400> SEQUENCE: 4
tgctgttgac agtgagcgct caaaagacaa ataatagtga agccacagat gtattatttg    60
gttatatctt ttgaatgcct actgcctcgg a                                  91

SELECTION OF HUMAN HEMATOPOETIC STEM CELLS USING EPCR

CROSS-REFERENCE TO RELATED APPLICATIONS

The present application is a U.S. National Phase of International Application No. PCT/CA2017/050661, filed on May 31, 2017 and claiming priority from U.S. Provisional Application No. 62/344,011 filed Jun. 1, 2016, the content of which are hereby incorporated by reference in their entirety.

TECHNICAL FIELD

It is provided a method of expanding hematopoietic stem cells by selecting a population of Endothelial Protein C Receptor cells.

BACKGROUND

Human hematopoietic stem cells (HSC) constitute a rare sub-population of cells with the unique ability to self-renew and differentiate into all blood lineages. Human cord blood (CB) is one of the most accessible sources for HSCs and is frequently used in clinical and research settings. HSCs in CB samples can be prospectively identified with high confidence using antibodies that detect the combinatorial surface expression of CD34, CD38, CD90, CD45RA and CD49f. With this approach, HSCs can be isolated to up to 10% purity from human CB units. Although representing several orders of magnitude of enrichment, the scarcity of HSCs in purified CB samples hampers the functional dissection of the molecular mechanisms underlying HSC self-renewal. One possible avenue to overcome this hurdle is to expand such rare cells ex vivo using recently developed tools such as the UM171 and other small molecules such as aryl hydrocarbon receptors antagonists, or fed batch bioreactor systems. Unfortunately, another issue associated with this strategy is the fact that several of the HSC markers described, for example CD38 and CD49f, are no longer reliable once HSCs are cultured. This significantly restricts the ability to assess the frequency and purify of HSCs in ex vivo culture conditions.

There is thus still need to be provided with a mean to improve purification of HSCs.

SUMMARY

In accordance with the present disclosure there is provided a method of expanding ex vivo stem and/or progenitor cells, the method comprising selecting a population of Endothelial Protein C Receptor (EPCR)$^+$ cells from a starting population of stem and progenitor cells, and culturing the selected EPCR$^+$ cells thereby expanding said EPCR$^+$ cells.

It is further provided a method of increasing ex vivo stem and/or progenitor cells, the method comprising selecting a population of Endothelial Protein C Receptor (EPCR)$^+$ cells from a starting population of stem and/or progenitor cells, and culturing the selected EPCR$^+$ cells thereby expanding said EPCR$^+$ cells.

It is also provided a method of expanding ex vivo stem and progenitor cells, the method comprising selecting a population of Endothelial Protein C Receptor (EPCR)$^+$ cells from a starting population of stem and/or progenitor cells, and culturing the selected EPCR$^+$ cells thereby expanding said EPCR$^+$ cells.

It is also provided a EPCR$^+$ cell population as expanded according to a method as defined herein.

It is further provided the use of a population of Endothelial Protein C Receptor (EPCR)$^+$ cells expanded by the method as defined herein for stem cells transplantation in a recipient.

It is additionally provided the use of Endothelial Protein C Receptor (EPCR)$^+$ cells expanded by the method as defined herein for treating a hematopoietic disorder/malignancy, an autoimmune disease and/or an inherited immunodeficient disease in a subject.

It is also provided a method of transplanting stem cells in a recipient comprising administering to the recipient a population of Endothelial Protein C Receptor (EPCR)$^+$ cells expanded by the method as defined herein.

It is also provided a method of treating a hematopoietic disorder/malignancy, an autoimmune disease and/or an inherited immunodeficient disease in a subject comprising administering to the a population of Endothelial Protein C Receptor (EPCR)$^+$ cells expanded by the method as defined herein.

It is further provided a filtering system for filtering a population of Endothelial Protein C Receptor (EPCR)$^+$ cells from a population of stem and/or progenitor cells comprising a matrix coated with an antibody specifically binding to an epitope of EPCR.

It is additionally provided a method of filtering stem and/or progenitor cells, the method comprising filtering a starting population of stem and/or progenitor cells to select a population of Endothelial Protein C Receptor (EPCR)$^+$ cells.

In an embodiment, the stem and progenitor cells are human hematopoietic stem cells (HSC).

In another embodiment, the stem and progenitor cells are human hematopoietic stem and progenitor cells.

In another embodiment, the hematopoietic stem cells are from umbilical cord blood cells, mobilized peripheral blood cells, or bone marrow cells.

In a further embodiment, the hematopoietic stem cells are mobilized peripheral blood cells.

In another embodiment, the hematopoietic stem cells are from human cord blood cells.

In a supplemental embodiment, the EPCR$^+$ cells are further enriched prior or after the selecting of the EPCR$^+$ cells by harvesting CD34$^+$, CD38$^+$, CD90$^+$, CD45RA$^+$, CD133 and/or CD49f$^+$ cells.

In a particular embodiment, EPCR$^+$ cells are further enriched prior or after the selecting of the EPCR$^+$ cells by harvesting CD34$^+$.

In an embodiment, the selected EPCR+ cells are CD34$^+$ CD45RA$^-$ CB cells.

In an additional embodiment, the hematopoietic stem cells are short and long term hematopoietic stem cells.

In another embodiment, the method described herein further comprises the step of stimulating the starting population with at least one cell expanding factor.

In a supplemental embodiment, the at least one cell expanding factor is UM171, UM729, or analogs thereof, lenalidomide, thalidomide or a combination thereof. In an embodiment, the at least one cell expanding factor is UM171. In another embodiment, at least one cell expanding factor is UM729.

In an embodiment, the method described herein further comprises stimulating the starting population with at least one cell expanding factor in combination with an aryl hydrocarbon receptor antagonist.

In another embodiment, the aryl hydrocarbon receptor antagonist is Stem Regenin 1 (SR1).

In a further embodiment, the EPCR$^+$ cells are expanded in a bioreactor.

In an embodiment, the stem and progenitor cells are expanded in combination with at least one cytokine.

In an embodiment, the at least one cytokine is selected from the group consisting of IL-1, IL-3, IL-6, IL-11, G-CSF, GM-CSF, SCF, FLT3 thrombopoietin (TPO), erythropoietin, analogs thereof, and a combination.

In another embodiment, the at least one cytokine is SCF, FLT-3, IL6, TPO, and a combination thereof.

In a further embodiment, the recipient is a human or an animal.

In another embodiment, the animal is a mouse.

In a particular embodiment, the hematopoietic disorder/malignancy, the autoimmune disease and/or the inherited immunodeficient disease comprise bone marrow failure conditions, lupus, acute myeloid leukemia, acute lymphoblastic leukemia, chronic myeloid leukemia, chronic lymphocytic leukemia, myeloproliferative disorders, myelodysplastic syndromes, multiple myeloma, non-Hodgkin's lymphoma, Hodgkin's disease, aplastic anemia, pure red cell aplasia, hemoglobinuria, Fanconi anemia, thalassemia, sickle cell anemia, Wiskott-Aidrich syndrome, or inborn errors of metabolism.

In another embodiment, the filtering system is a column or beds.

In an embodiment, the starting population of stem and/or progenitor cells is filtered through a filtering system as defined herein.

In a particular embodiment, the filtering system is Clinimacs®, EasySep™, RoboSep™, RosetteSep™, or StemSep™.

It is also provided the use of Endothelial Protein C Receptor (EPCR)$^+$ cells expanded by the method described herein or the EPCR$^+$ cell population as described herein for treating a subject in need of a treatment with cell gene therapy, wherein the EPCR$^+$ cells or EPCR$^+$ cell population are infected with a viral vector comprising a nucleic acid encoding a gene of interest.

It is also provided a method of expressing a gene of interest in a cell, comprising the step of infecting Endothelial Protein C Receptor (EPCR)$^+$ cells expanded by the method or the EPCR$^+$ cell population as described herein with a vector comprising a nucleic acid encoding a gene of interest.

It is further provided a method of expanding ex vivo stem and/or progenitor cells, the method comprising selecting a population of CD34$^+$, CD38$^+$, CD90$^+$, CD45RA$^+$, CD133 and/or CD49f$^+$ cells; selecting a population of EPCR+ cells from the CD34+ cells; and culturing the selected EPCR$^+$ cells thereby expanding the EPCR$^+$ cells.

In an embodiment, the method described herein comprises a first step of selecting a population of CD34$^+$ cells.

In an embodiment, the stem and progenitor cells, the selected cells or the EPCR+ cells are stimulated with UM171.

BRIEF DESCRIPTION OF THE DRAWINGS

Reference will now be made to the accompanying drawings.

FIG. 1 illustrates cultured CD49f$^{high}$ CD34$^+$CD45RA$^-$ cells lack in vivo repopulating potential.

FIG. 4 illustrates that EPCR is a universal surface marker for LT-HSC in culture.

FIG. 6 illustrates the frequency of LT-HSC within EPCR$^-$, EPCR$^{Low}$ and EPCR$^+$ populations. FIG. 6A is a table summarizing limit dilution analysis of the indicated sorted populations. CD34$^+$CD45RA$^-$ cells were expanded for 7 days in the presence of UM171 (38 nM). Five cell doses and their respective fractions based on EPCR expression (−, low, and +) were sorted and transplanted in NSG (n=5 mice per dose, technical replicates). The number of engrafted/transplanted mice (E/T) with the average of human CD45 reconstitution is presented. Number of LT-HSCs per 103 CD34$^+$CD45RA$^-$ starting cells based on the estimated LT-HSC frequencies and 95% clearance (Cl).

FIG. 8 illustrates the in vivo proliferative outcome of different HSPC populations sorted after culture.

FIG. 9 illustrates that expanded EPCR$^+$ progeny retains the most of the ex vivo HSPC expanded cells.

FIG. 10 illustrates that EPCR$^+$ cells do not emerge from EPCR$^-$ isolated fraction.

FIG. 11 illustrates that uncultured EPCRlow and EPCR+ population are the fractions enriched with LT-HSC.

FIG. 12 illustrates the loss of EPCR expression in CD34$^+$ cells compromise their engraftment ability in NSG mice.

FIG. 13 illustrates that the loss of EPCR expression in CD34$^+$ cells compromise their engraftment ability in NSG mice.

FIG. 15 illustrates that EPCR$^+$ population shares genetic features with highly purified primitive hematopoietic cells.

DETAILED DESCRIPTION

In accordance with the present disclosure, there is provided a method of expanding stem and/or progenitor cells, the method comprising selecting a population of Endothelial Protein C Receptor (EPCR)+ cells and expanding the cells.

Cell purification technology combined with transcriptome sequencing and a small molecule agonist of hematopoietic stem cell self-renewal have allowed to identify the endothelial protein c receptor (EPCR) as a surface marker that defines a rare subpopulation of human cells highly enriched for stem cell activity in vivo. EPCR-positive cells exhibit robust multi-lineage differentiation potential and serial reconstitution ability in immunocompromised mice. Following ex vivo stem cell expansion, HSC activity is detected in EPCR$^+$ subpopulations, arguing for the stability of this marker on the surface of cultured cells, a feature not commonly observed with other recently described markers. Functionally, EPCR is essential for human HSC activity in vivo. Cells engineered to express low EPCR levels lack the ability to confer long-term reconstitution.

Encompassed herein are stem and progenitor cells being human hematopoietic stem cells (HSC). The hematopoietic stem and progenitor cells encompassed herein can be from umbilical cord blood cells, mobilized peripheral blood cells, or bone marrow cells.

Transcriptome analysis of CD34-enriched human CB cells expanded ex vivo revealed the Endothelial Protein C Receptor (EPCR) gene as one of the best determinants of HSPCs response to UM171 (see U.S. patent application Ser. No. 14/374,953, incorporated herein by reference in its entirety), which stimulates human hematopoietic stem and progenitor cell (HSPC) expansion in vitro.

Hematopoietic stem cells (HSCs) also refer to long term HSC (LT-HSC) and short term HSC (ST-HSC). LT-HSC and ST-HSC are differentiated, based on their cell surface marker expression. In addition, ST-HSC are less quiescent (i.e., more active) and more proliferative than LT-HSC. However, LT-HSC have unlimited self-renewal (i.e., they survive throughout adulthood), whereas ST-HSC have limited self-renewal (i.e., they survive for only a limited period of time).

Figure 1A:
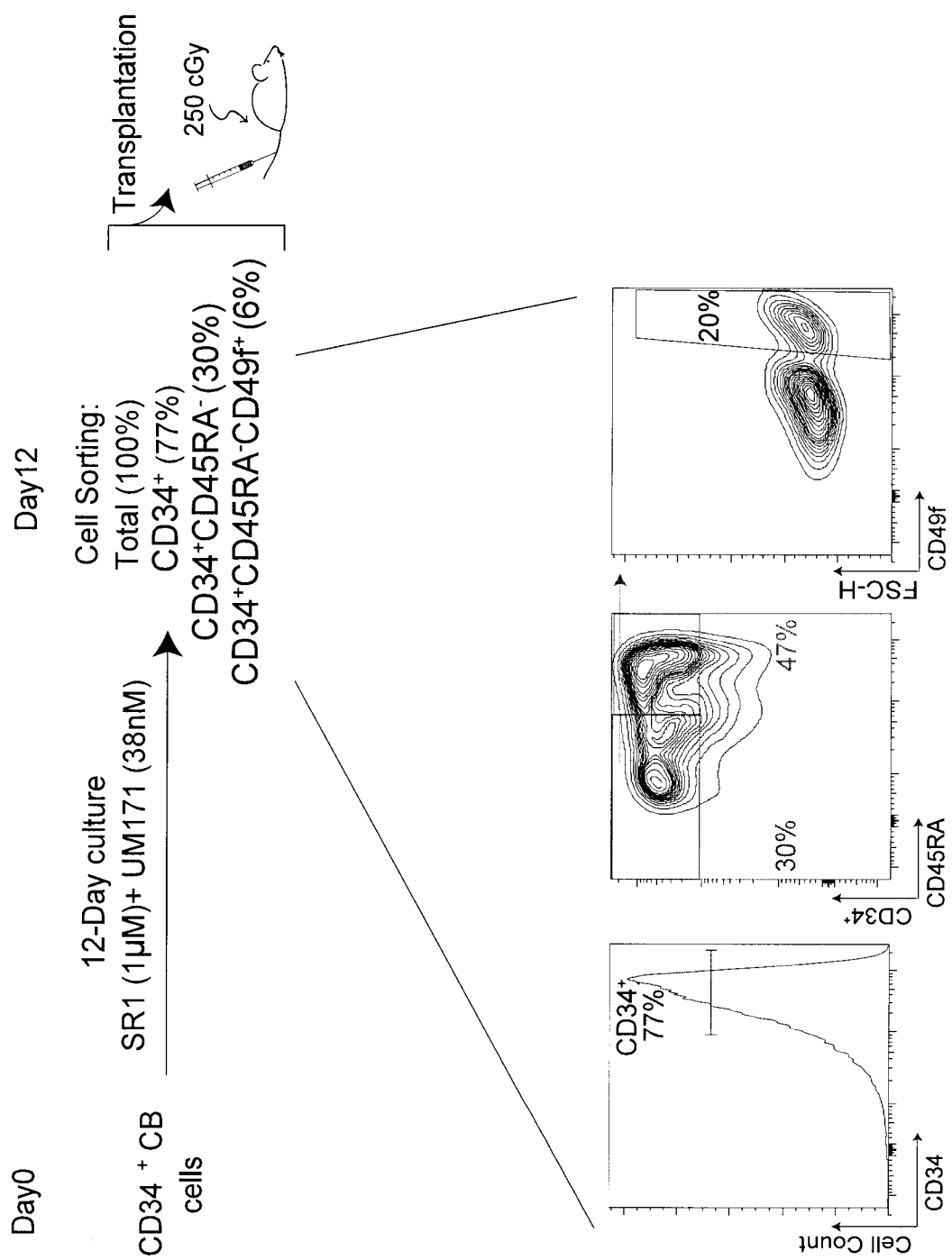
FIG. 1A is a schematic presentation of HSPC phenotype sort and transplantation strategy. CD34$^+$ cord blood (CB) cells were expanded for 12 days in SR1 (1 μM) +UM171 (38 nM) before they were sorted for the indicated populations.
Figure 1B:
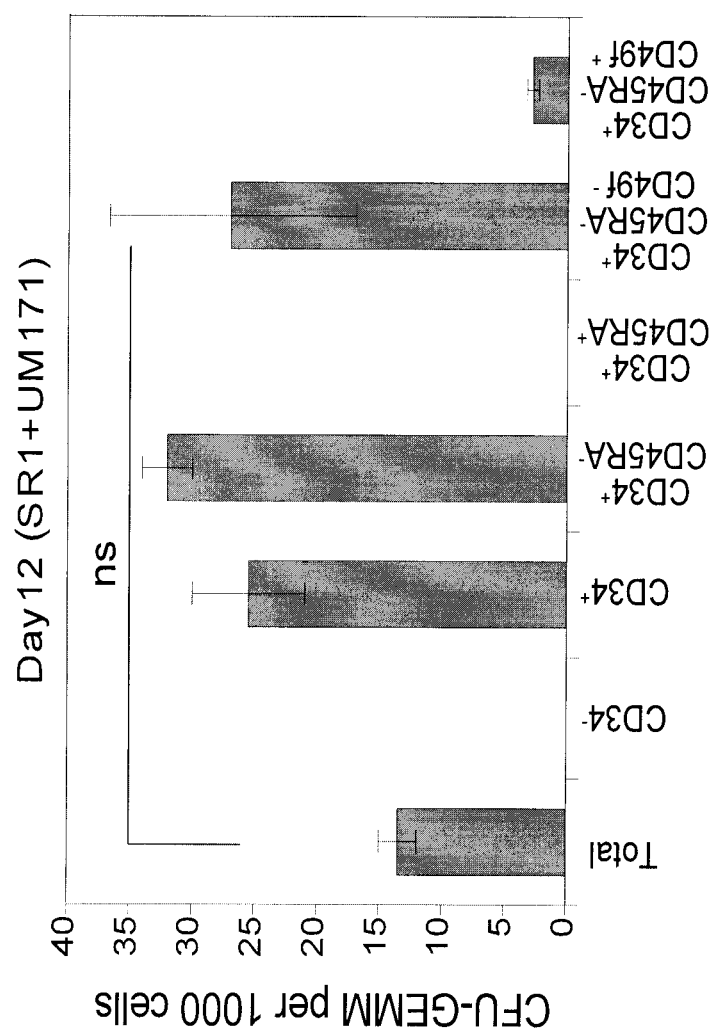
FIG. 1B shows CFU-GEMMs count for different cellular subsets after culture (mean±s.d, n=3 wells counted per condition, technical replicates). Comparison between various sorted populations to Total sorted cells is statistically significant difference unless specified ns: not significant (Mann-Whitney test, one-sided).
Figure 1C:
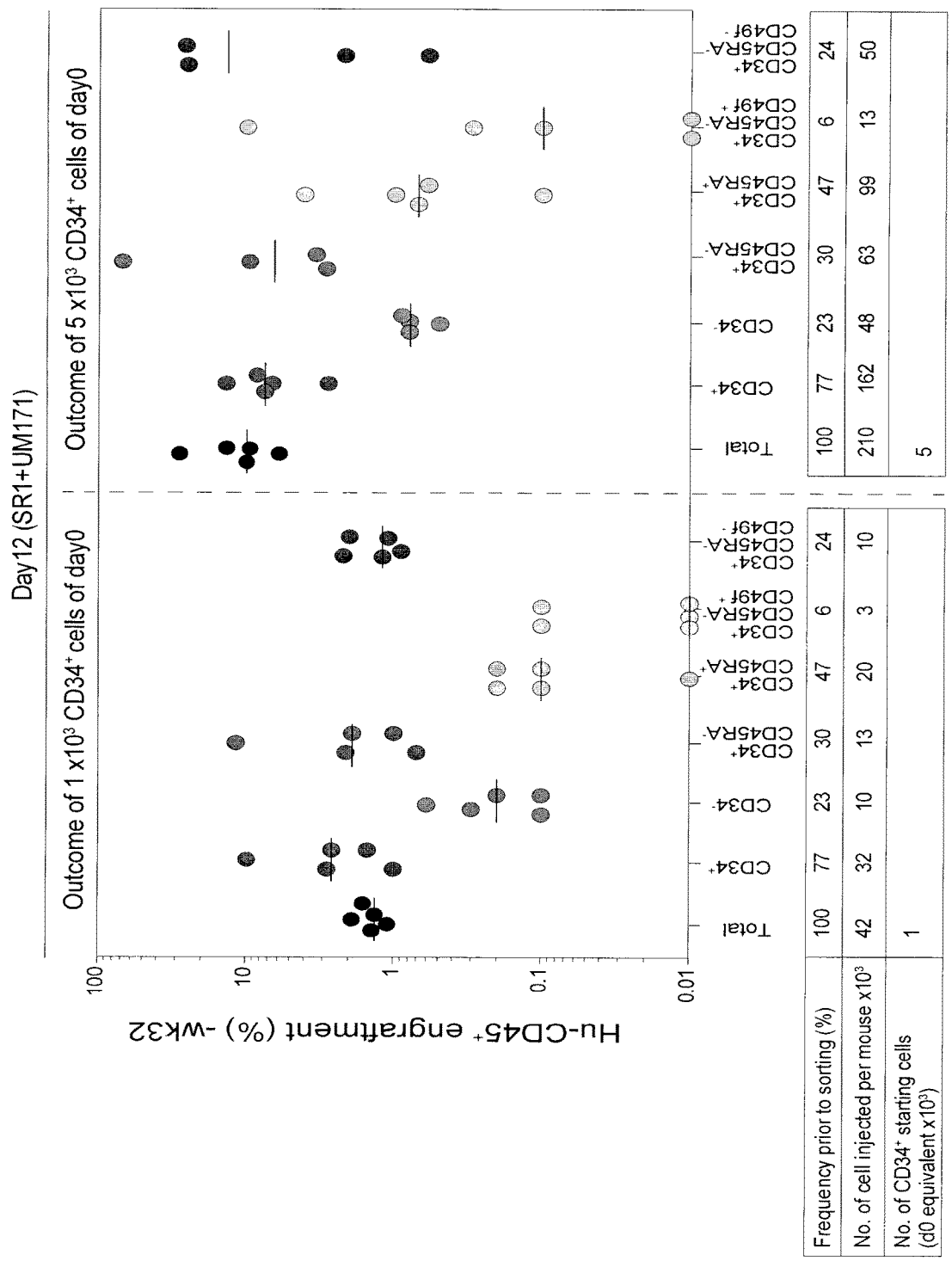
FIG. 1C reports representative FACS purified populations were transplanted in NSG mice for outcome of 1 and 5×103 CD34+CB starting cell. Proportion of cultured cells transplanted for each cellular subset was adjusted based on their frequency at day 12 and indicated in the table of panel. Bone marrow analysis was performed at 32 weeks post-transplantation (n=5 mice per condition, technical replicates). The horizontal bars indicate the median values.

As previously described and demonstrated in FIG. 1 herein, the low HSC frequency in biological specimens as well as the inability to purify HSCs to homogeneity has challenged the molecular characterization of these cells. HSC frequencies of 1 in 10-20 can be achieved by depleting CD38 and CD45RA-expressing cells from uncultured human cord blood (CB) units and enriching for CD34, CD90, and CD49f expressing cells, however relying on these markers to evaluate HSC activity in vitro is not feasible since the expression of these markers changes dramatically when cells are introduced in culture (FIG. 1).

Figure 2:
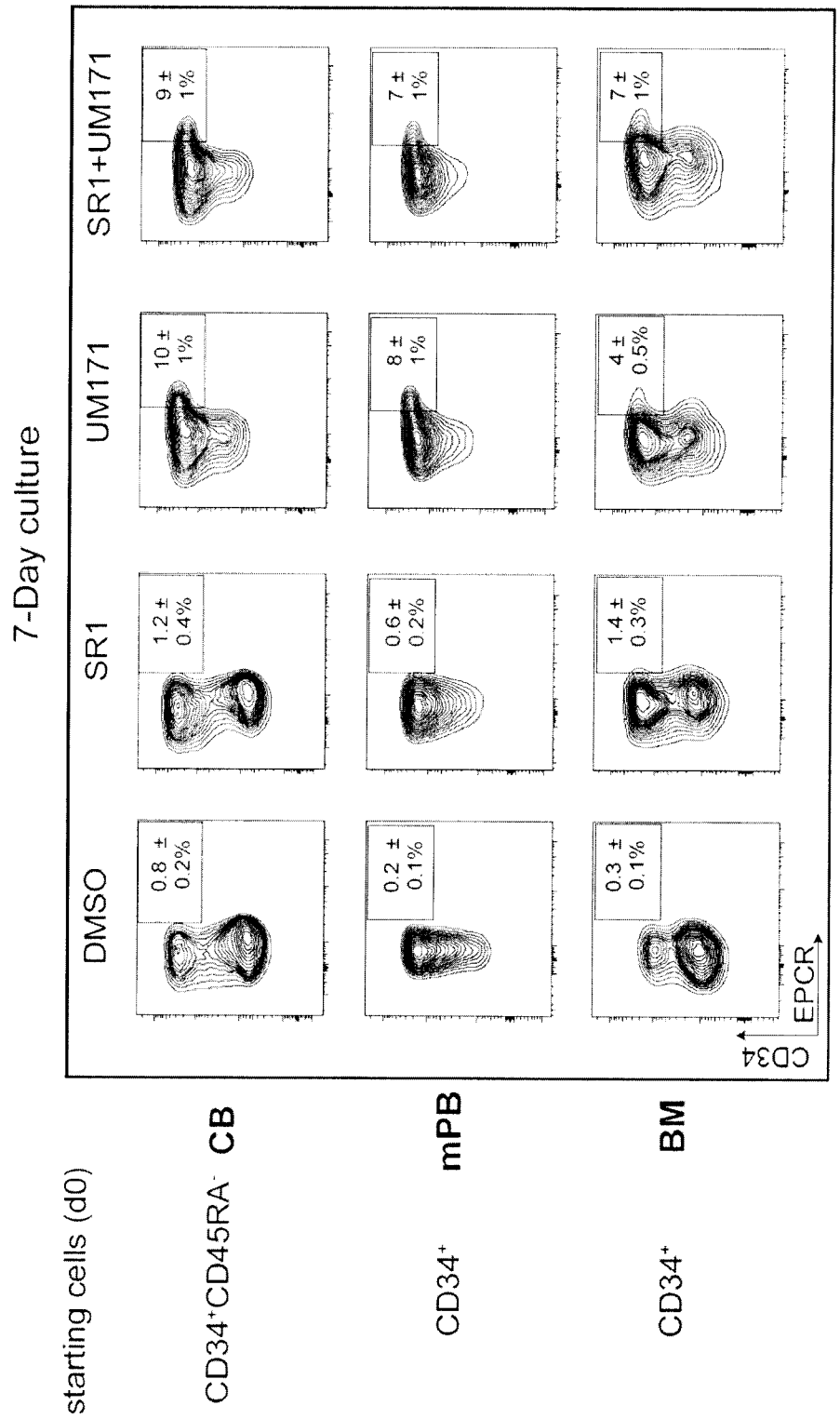
FIG. 2 illustrates CD34+ cells expanded with UM171 retain higher levels of EPCR surface marker expression than those expanded with SR1 irrespective of HSPC source. Representative flow cytometry plots for CD34 and EPCR expression. Cord blood (CB), mobilized peripheral blood (mPB), and bone marrow (BM)-derived CD34+ or CD34+ CD45RA cells cultured for 7 days in the presence of vehicle (DMSO), UM171 (38 nM), and SR1 (1000 nM). Data presented as mean±s.d for 3 technical replicates.

Exposure of cord blood (CB)-derived CD34+ cells to UM171 leads to a rapid induction of EPCR expression both at the mRNA (12 hrs) and protein (24 hrs) level. This effect is further confirmed following expansion of CB CD34$^+$ cells for 7 days with UM171 using different clones of the EPCR antibody and different sources of human hematopoietic cells, such as mobilized peripheral blood (mPB) and bone marrow (BM) (FIG. 2). Interestingly, although exposure of CB, mPB or BM cells to the AhR antagonist SR1, a small molecule promoting the ex vivo expansion of CD34+ cells, produces a small increase in the proportion of EPCR+ cells (most likely due to an overall expansion of the CD34+ population), the most substantial and consistent increase in EPCR expression for these cells was observed upon UM171 treatment (FIG. 2). As expected, no significant additive effect was noted when cultures were treated with both UM171 and SR1 (FIG. 2). Moreover, although both the EPCR−CD34$^+$ and EPCR$^+$CD34$^+$ populations are comprised within the CD34$^+$CD38$^-$ and CD49f$^{Med}$ subsets, which represent typical phenotypes of fresh HSCs, only the EPCR$^+$CD34$^+$ population expresses CD90 and CD133, indicating that EPCR positivity defines a subset of HSCs with a more primitive phenotype (i.e. CD34$^+$CD38$^-$ CD49f$^{med}$CD90$^+$CD133$^+$).

Figure 3A:
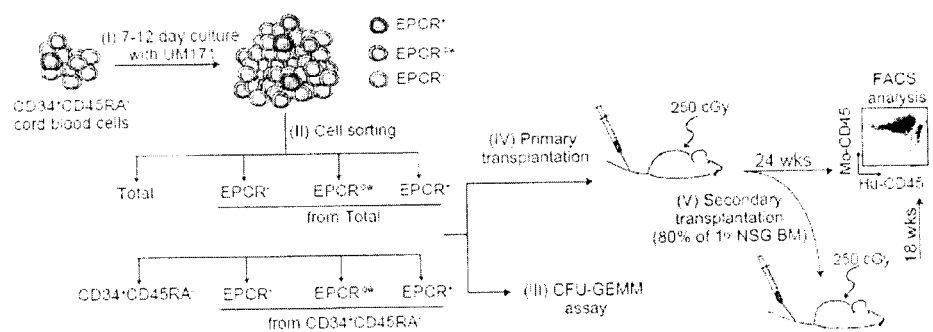
FIG. 3A shows a schematic representation of EPCR sort after 7 and 12-day culture in UM171 (38 nM).

To evaluate if EPCR expression correlates with HSC activity, UM171-treated cultures initiated 7 and 12 days earlier with CD34$^+$CD45RA$^-$ CB cells were sorted based on EPCR expression levels (EPCR$^-$, EPCR$^{low}$ and EPCR$^+$) and their HSPC content was monitored (FIG. 3A, B).

Figure 3B:
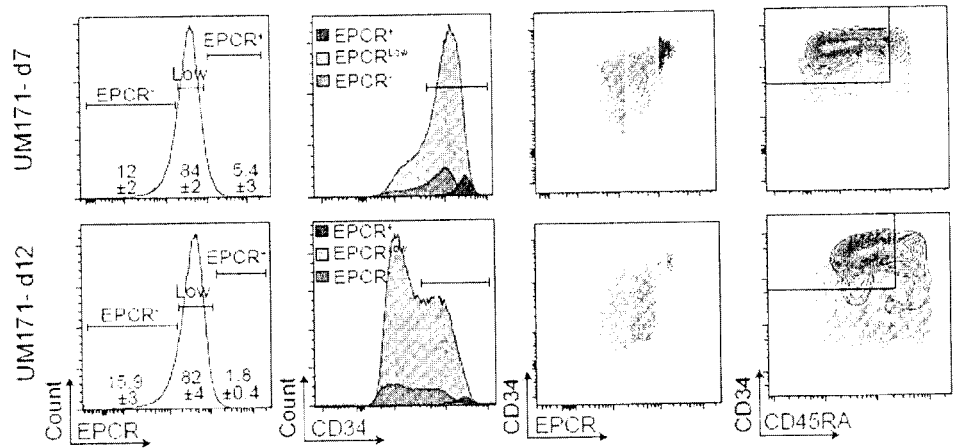
In FIG. 3B, FACS plot showing the percentage of EPCR subsets and their distribution in CD34$^+$ and CD34$^+$ CD45RA$^-$ cells after culture (mean±s.d, 5 biological replicates) are seen.
Figure 3C:
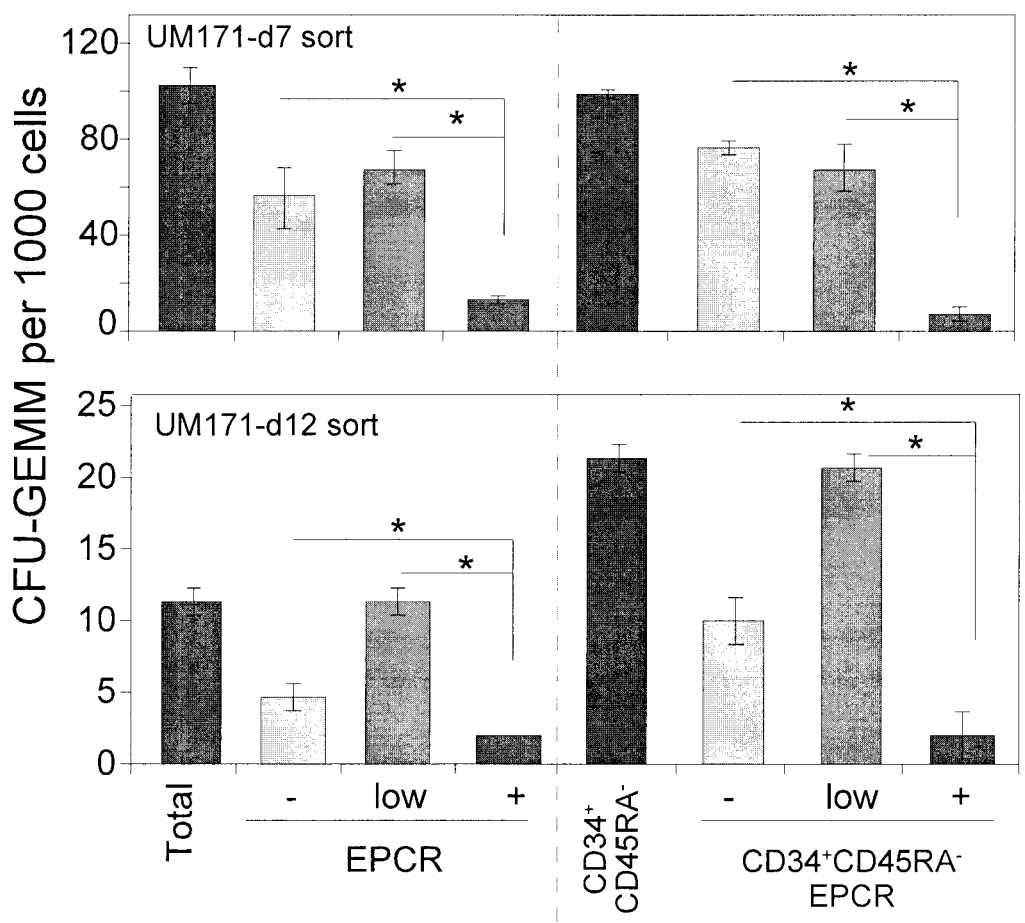
FIG. 3C shows CFU-GEMMs count for EPCR sorted subsets after culture (mean±s.d, n=3 wells counted per condition of 2 biological replicates); significance level *P<0.05 (Mann-Whitney test, one-sided). Human (Hu) CD45 engraftment and lineage potential of the indicated sorted cells assessed for each NSG recipient mouse identified as NSG-ID after 7- (FIG. 3D) and 12-(FIG. 3E) day culture; n=3-20 mice per condition (each geometric shape corresponds to a biological replicate).
Figure 3D:
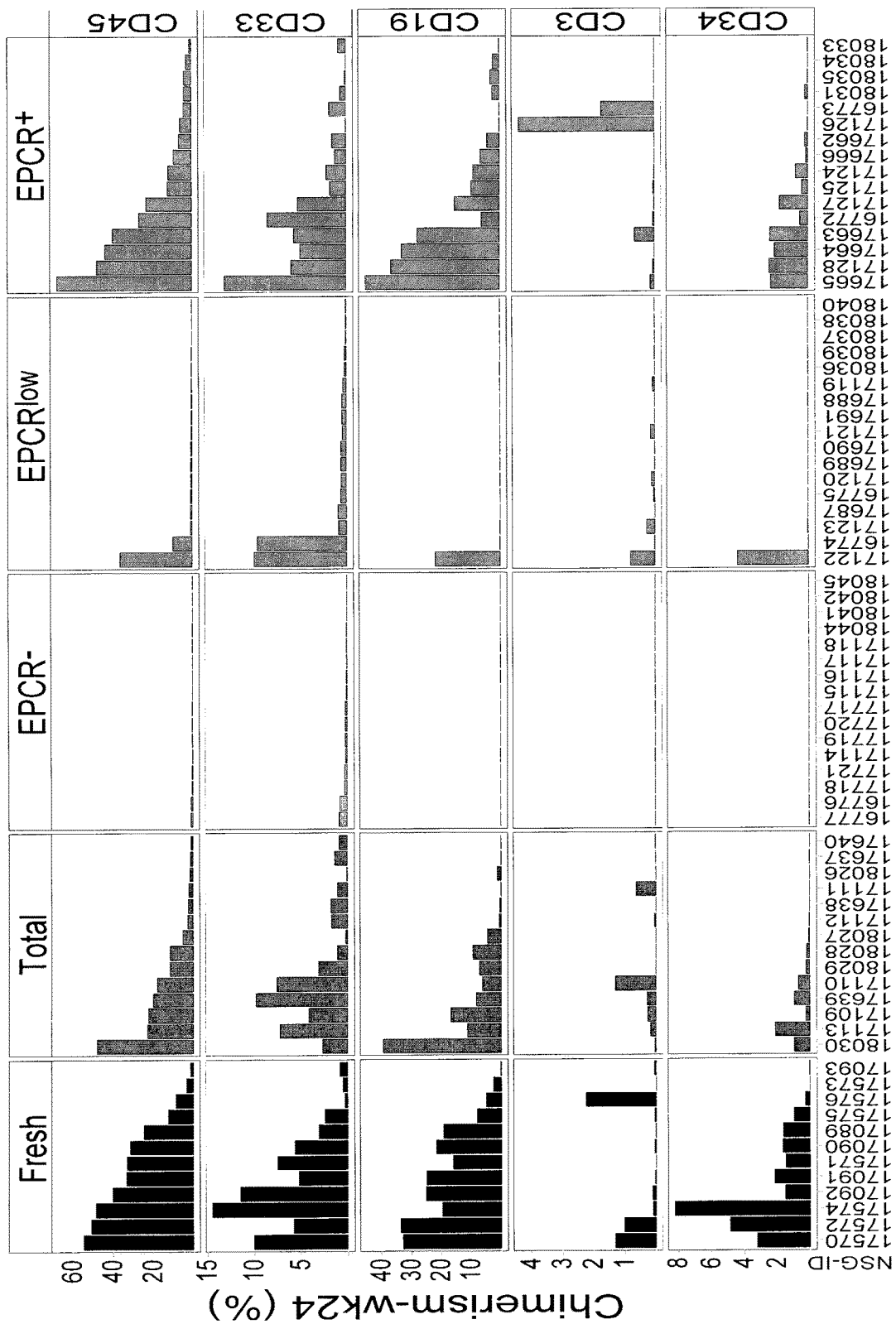
FIG. 3 illustrates that the EPCR$^+$ population is enriched with LT-HSC in culture.
FIG. 3F shows primary NSG mice, receiving the indicated sorted population after 7 and 12 day culture from 3×103 CD34$^+$CD45RA$^-$ starting cell (d0 equivalent), were transplanted into 2ry NSG recipients. Hu-CD45 cell chimerism was analyzed in the 1ry and 2ry mice at 24 and 18 weeks posttransplantation respectively by flow cytometry; n=4-5 mice per condition, technical replicates.
Figure 3E:
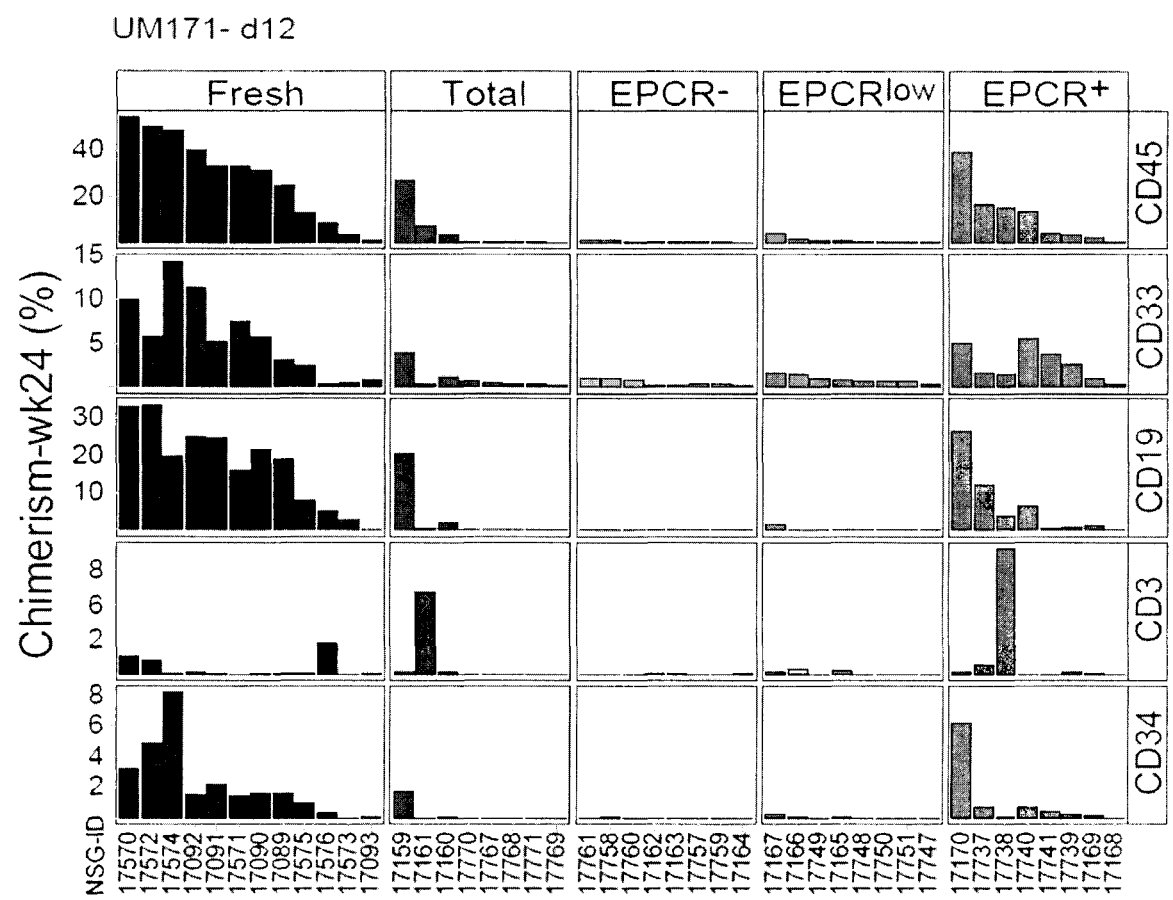
Figure 7:
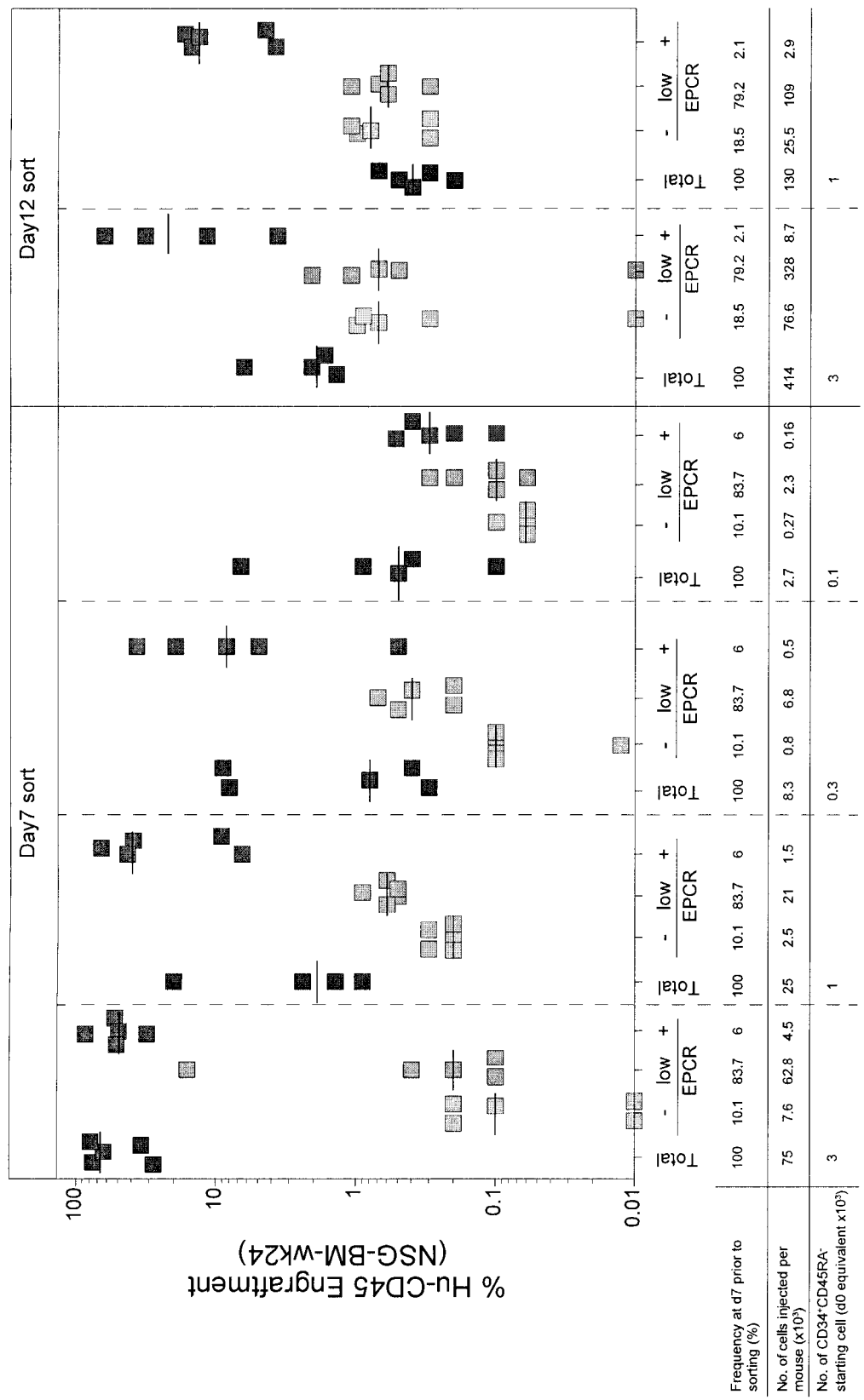
FIG. 7 illustrates the limit dilution assay performed on different EPCR cellular fractions (−, low, and +). CD34$^+$CD45RA$^-$ (d0 starting) cells were cultured for 7 and 12 days in the presence of UM171. Cells then were sorted based on EPCR expression at the day of culture. Outcome of 4 and 2 doses of the d0 starting cells were used after 7 and 12 day culture, respectively. The sorted cells were injected in sublethally irradiated NSG mice (n=5 mice per dose, technical replicates). Levels of human (Hu) CD45 engraftment in NSG bone marrow (BM) at 24 weeks post-transplantation is shown. The horizontal bars indicate median values.

At day 7 and 12, the EPCR$^+$ subpopulation represented 5±3% and 1.8±0.4% of the culture, respectively, and showed elevated CD34 expression (FIG. 3B). The EPCR$^+$ population was less clonogenic than the EPCR$^{low}$ and EPCR$^-$ populations, as illustrated by the difference in frequencies of CFU-GEMM between these subsets (FIG. 3C). In sharp contrast, the long-term reconstitution activity of the cultured cells was essentially restricted to the EPCR$^+$ subpopulation both at day 7 and at day 12 (FIG. 7). The strength of this marker to identify expanded LT-HSCs in culture is further highlighted by the relative enrichment of these cells as the culture progresses, from 20-fold enrichment at day 7 to 56-fold by day 12 (FIG. 7). In addition to their long-term reconstitution potential, EPCR expressing cells exhibited multi-lineage engraftment (FIG. 3D). Not only does EPCR expression correlate with LT-HSC activity in vivo at 24 weeks, it also identifies LT-HSCs with multi-lineage potential (FIG. 3D, E). These results were reproduced in a second series of experiments in which similar EPCR-based cell sorting was performed from CD34⁺CD45RA⁻ cells as compared to bulk cultures (FIG. 7).

Figure 4A:
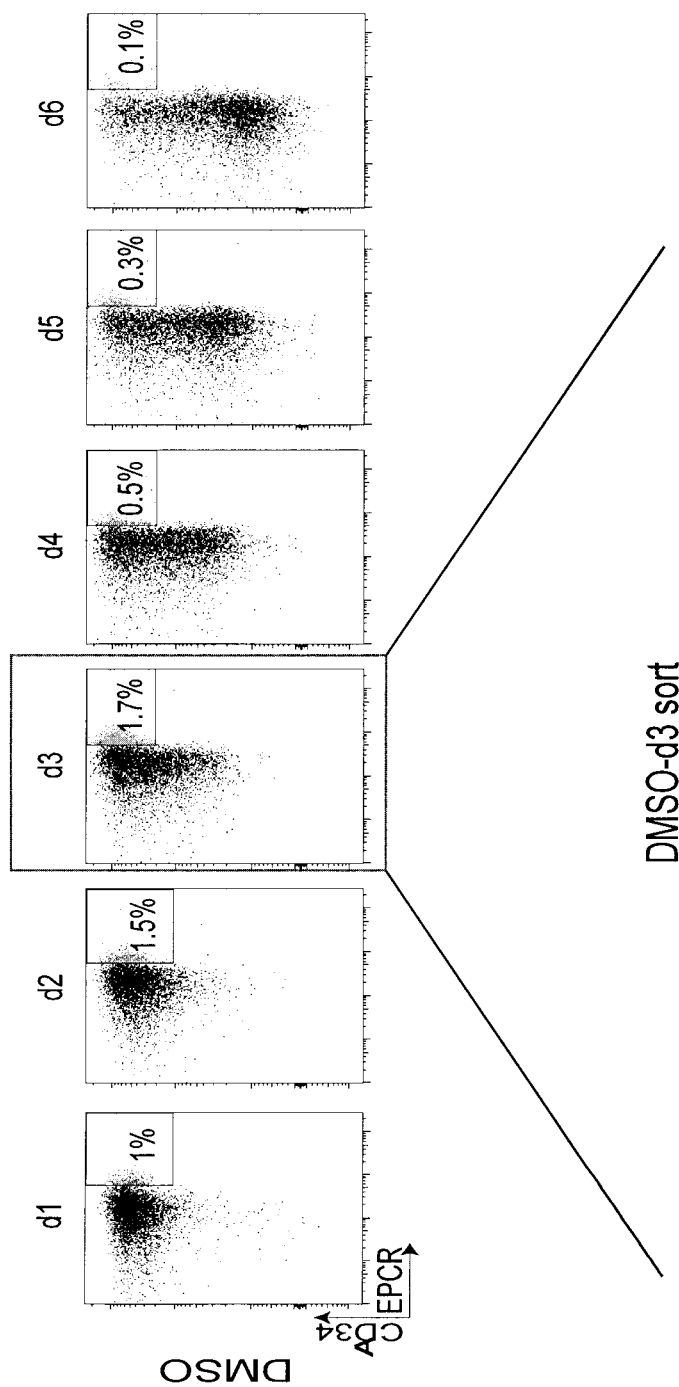
FIG. 4A shows that CD34$^+$CD45RA$^-$ CB cells were cultured in DMSO for 6 days. FACS analysis of EPCR kinetic expression was monitored during the culture period where the highest level of EPCR was attained at day 3.
Figure 4B:
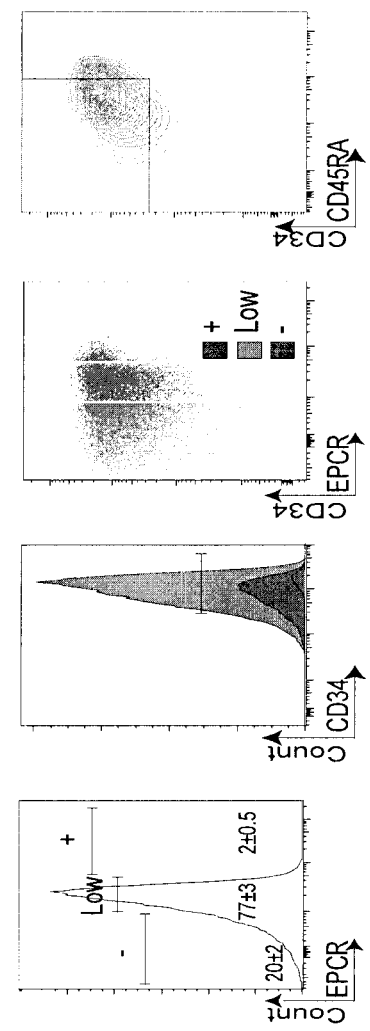
FIG. 4B illustrates that EPCR cell sorting scheme and phenotype after 3 day culture in DMSO controls (mean±s.d, 3 biological replicates).
Figure 4C:
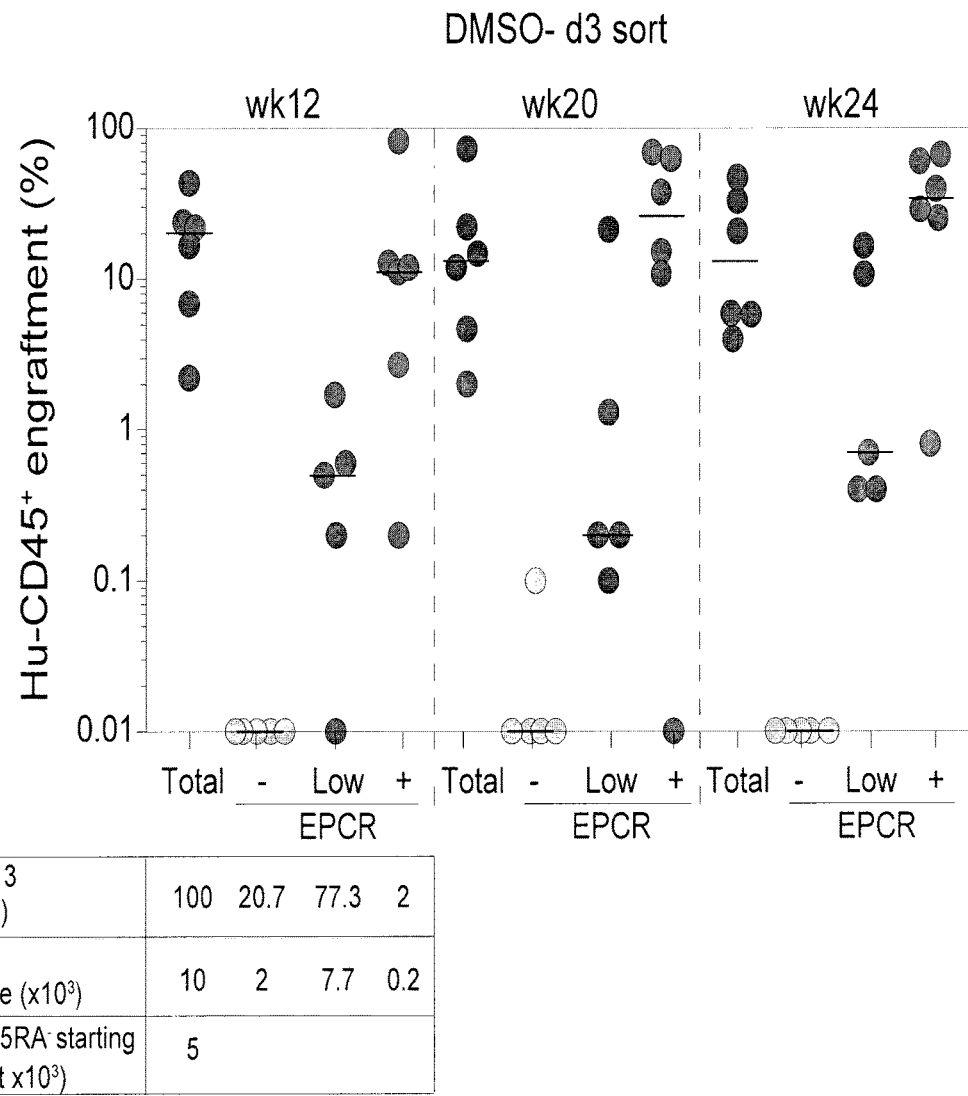
FIGS. 4C and 4D shows Human (Hu) CD45 engraftment and lineage potential of the indicated sorted cells assessed in NSG mice at 12, 20, and 24 weeks post-transplantation; n=5-6 mice per condition, technical replicates.
Figure 4D:
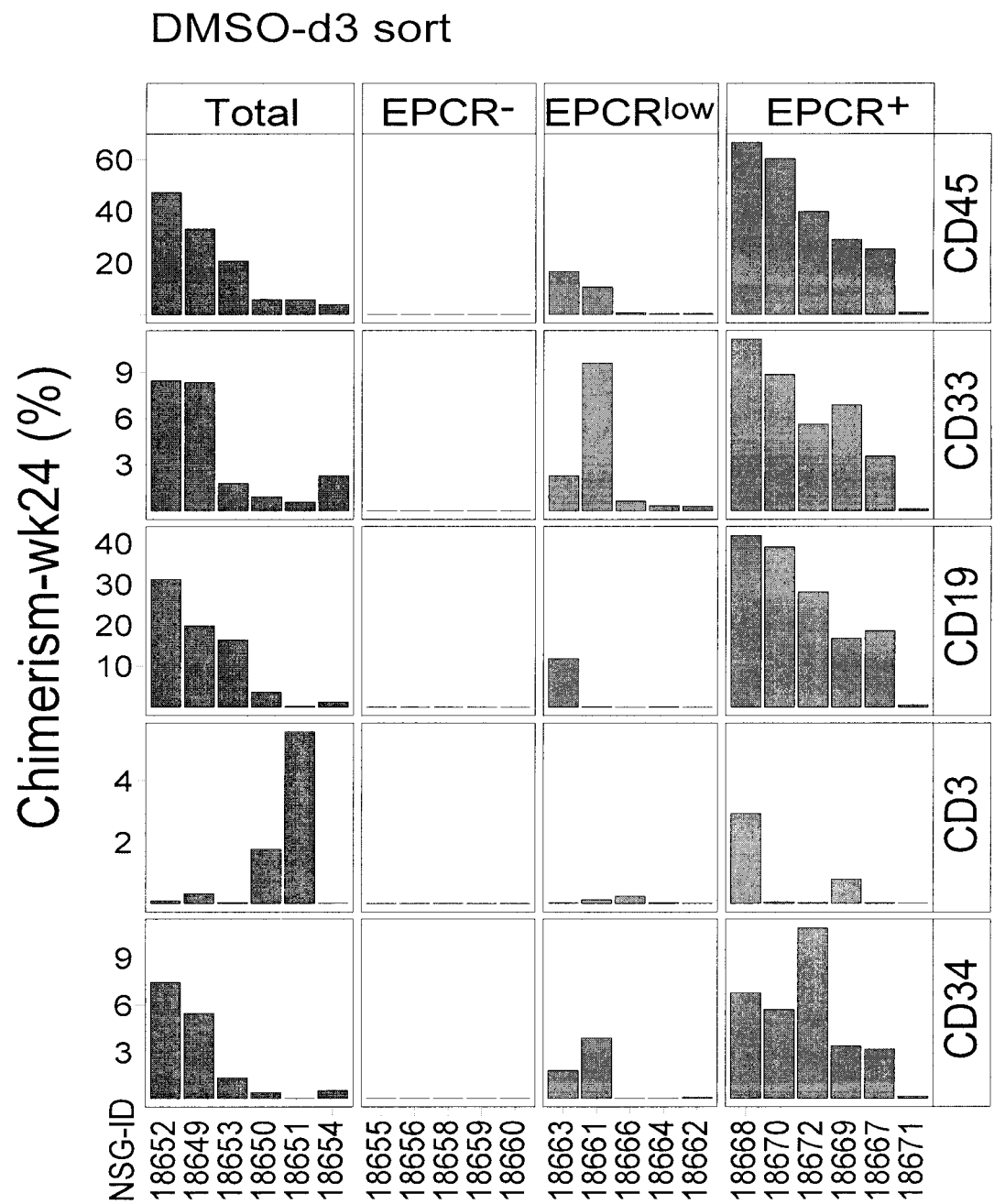
Figure 5:
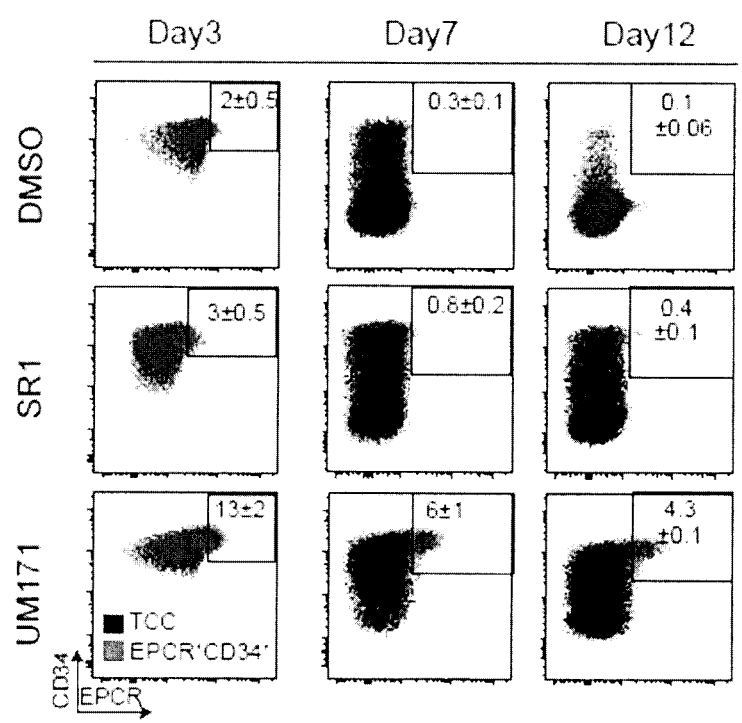
FIG. 5 illustrates that CD34$^+$CB cells expanded with UM171 retain higher levels of EPCR surface marker expression than those expanded with SR1. Representative flow cytometry plots of CD34 and EPCR of CD34$^+$B cells after 3, 7 and 12 days in the presence of vehicle (DMSO), UM171 (38 nM), and SR1 (1000 nM) (mean±s.d, 3 technical replicates) are seen.

It is also disclosed that EPCR is a reliable HSC marker in experimental conditions where CB cells are not exposed to UM171. For these experiments, CD34⁺CD45RA⁻ CB cells were sorted based on EPCR expression after 3 days in culture, at which time LT-HSCs are still detectable and EPCR expression is maximal (FIG. 4A). Accordingly, EPCR⁺ cells from DMSO-treated cultures were characterized by long-term repopulating activity and multi-lineage potential similar to bulk cells (see FIG. 4C, D), demonstrating that EPCR identifies expanded CB cells with LT-reconstitution potential in culture, irrespective of the presence of UM171.

Based on these results, EPCR can be used as a surrogate maker to predict LT-HSC enrichment in different culture conditions. To test this, EPCR⁺CD34⁺ cells was monitored in UM171 or SR1-treated cultures after 12-day expansion where LT-HSC frequency was previously shown to be 13-fold higher in UM171-treated cultures compared to SR1. Interestingly, EPCR⁺CD34⁺ cells were up to 10 times more abundant in cultures treated with UM171 when compared to those supplemented with SR1 (FIG. 7). Altogether, these results show that EPCR is a suitable marker to identify HSCs, irrespective of the culture condition.

Figure 6B:
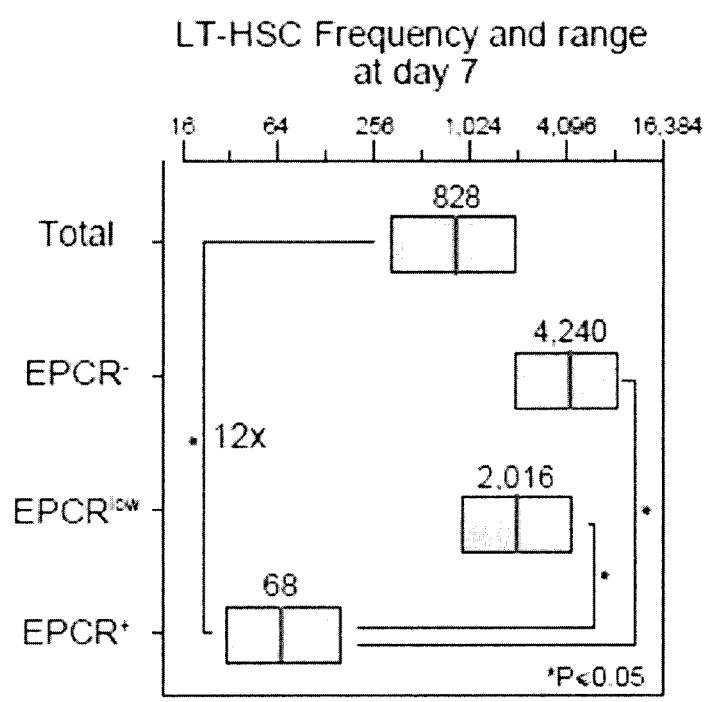
FIG. 6B shows the estimated LT-HSC frequencies (red lines) and 95% Cl (gray boxes) presented as 1/number of sorted cells at day 7; significance level *P<0.05 (Mann-Whitney test, one-sided).

EPCR⁺ cells was a multipotent LT-HSC in UM171 supplemented cultures harvested at day 7. The LT-HSC frequency was lower in all other fractions ranging from 1 per 2016 cells in EPCR$^{low}$ to 1 per 4240 cells in EPCR subpopulations (FIG. 6A, 6B). Considering the LT-HSC frequency in the unsorted expanded CD34⁺CD45RA⁻ culture, it was calculated that sorting on EPCR alone provided a 12-fold net enrichment in LT-HSCs (FIGS. 6A and 6B, and FIG. 7).

Figure 3F:
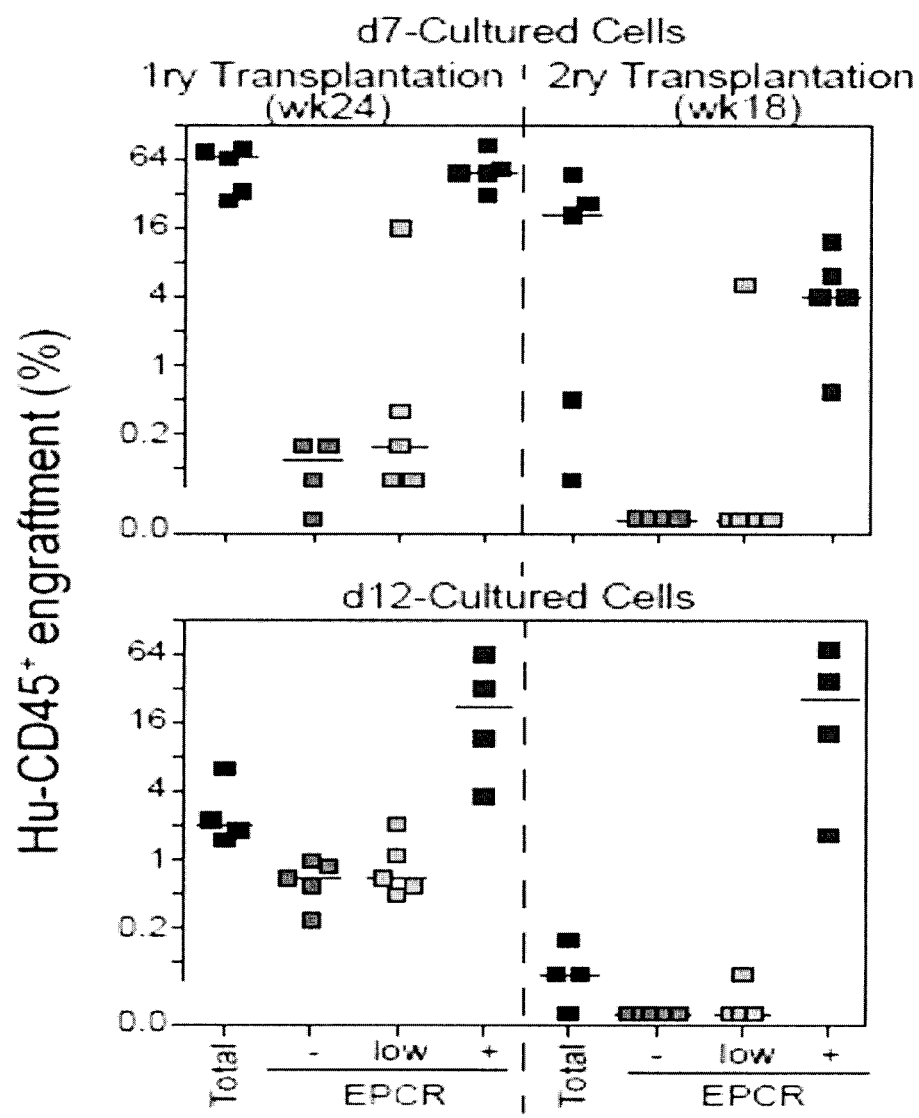

To further evaluate the self-renewal potential of each EPCR subset, a secondary transplantation experiments was performed in which cells collected 24 weeks post transplantation from bone marrow (BM) of primary mice were transplanted into secondary recipients and monitored for an additional 18 weeks. As shown in FIG. 3F, reconstitution of secondary recipients was limited to mice transplanted with grafts originating from either unsorted cells or EPCR⁺ cells derived from the day 7 (FIG. 3F, upper panel) or day 12 cultures (FIG. 3F, lower panel). Secondary recipients of the marrow from EPCR⁻ or EPCR$^{low}$ primary donors showed very low levels of engraftment, which was frequently undetectable. These findings show that only EPCR⁺ cells possess the required self-renewal potential to provide long-term multipotent reconstitution in serial transplantation settings.

Figure 8A:
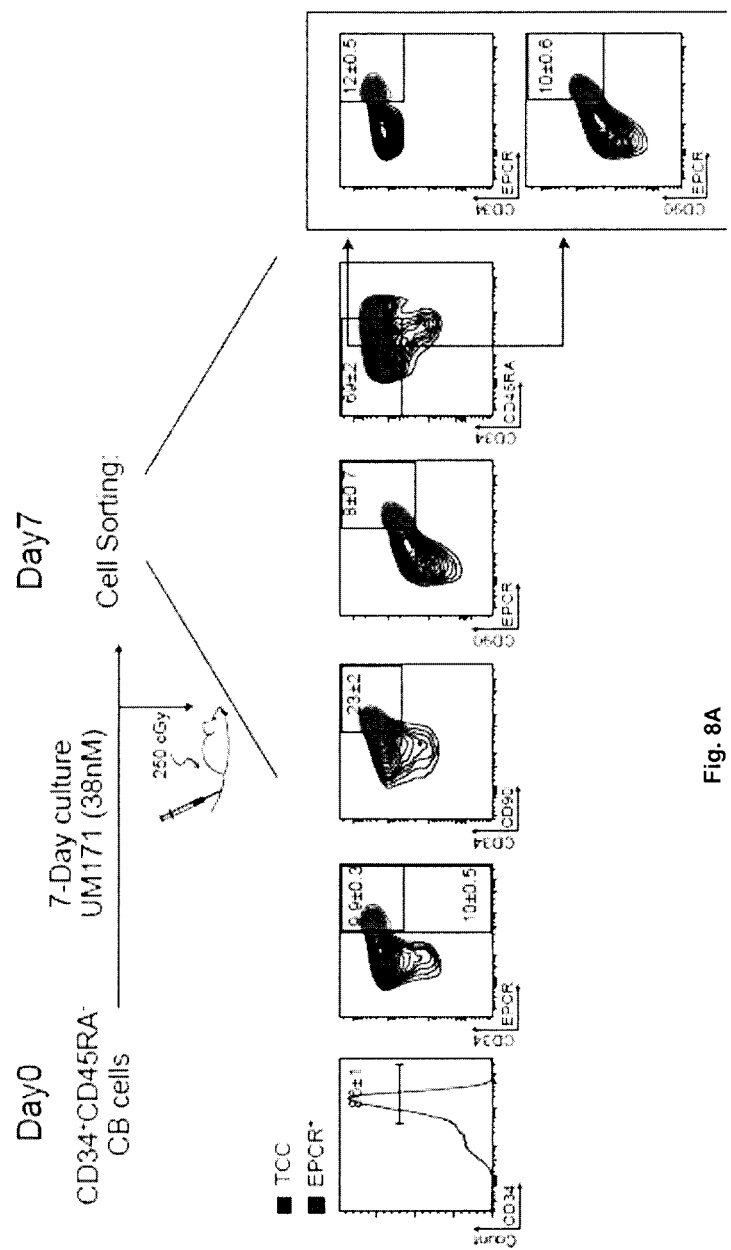
FIG. 8A is a schematic presentation of HSPC phenotype sort and transplantation strategy. CD34$^+$CD45RA$^-$ cord blood (CB) cells were expanded for 7 days in UM171 (38 nM) before they were sorted for the indicated HSPC population (mean±s.d, 3 technical replicates).

A combinatorial surface marker-based sorting approach might improve the ability to isolate LT-HSCs, and thus analyzed EPCR expression in combination with CD90 and CD45RA. To this end, CD34⁺CD45RA⁻ CB cells were kept in UM171-supplemented culture for 7 days and then sorted into 7 different fractions based on CD34, EPCR, CD45RA and CD90 expression (FIG. 8A). Each fraction was then transplanted in NSG mice and reconstitution was analyzed at early (3 weeks) and late (24 weeks) time points (FIG. 8B).

Figure 8B:
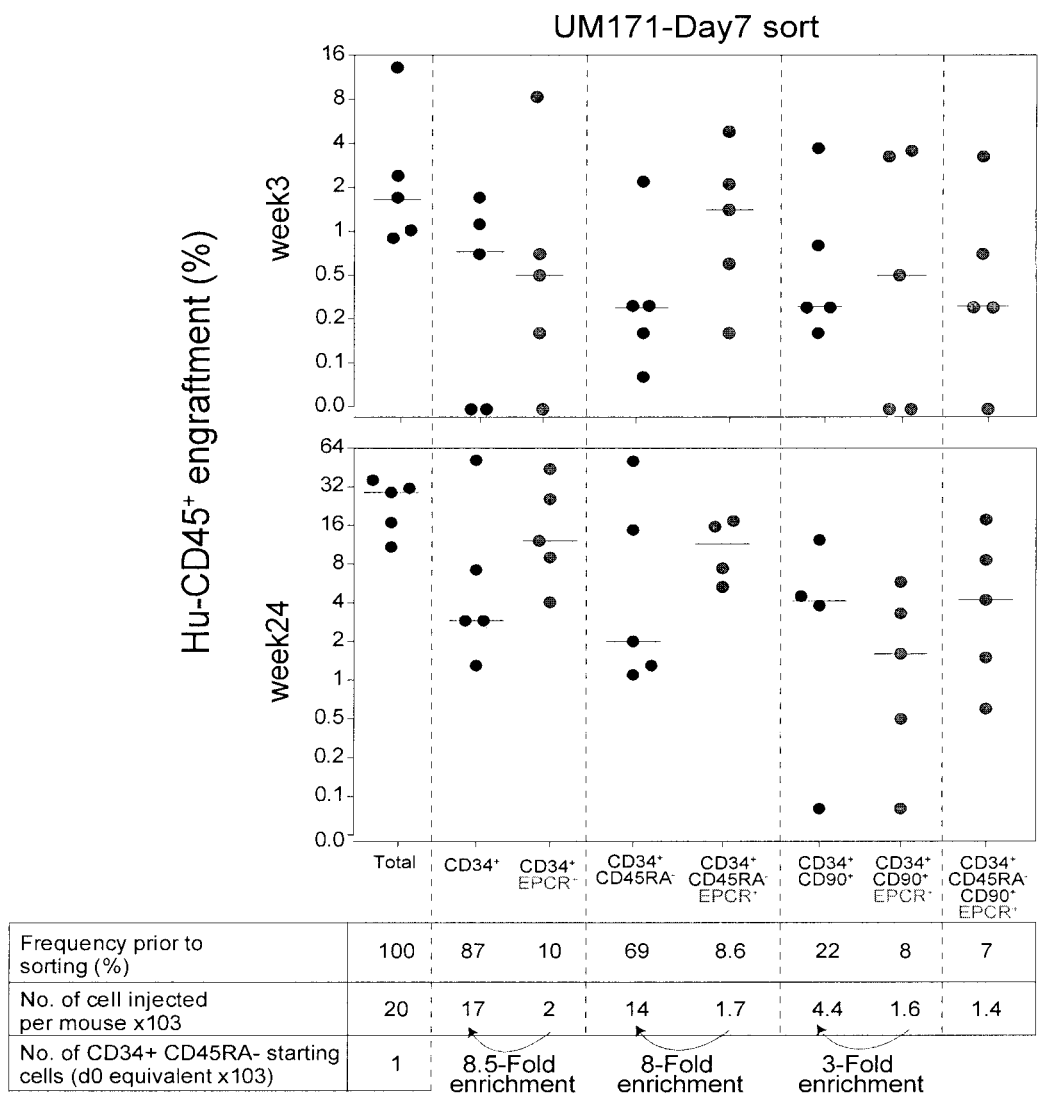
FIG. 8B shows the respective HSPC populations based on their frequency at day 7 were sorted and transplanted in NSG mice for outcome of 1×103 CD34$^+$CD45RA$^-$ CB starting cell. Bone marrow analysis was performed at 3 and 20 weeks post-transplantation to determine the short and long-term engraftment respectively; n=5 mice per condition, technical replicates. The horizontal bars indicate median values.

In an embodiment, selection of CD34⁺ cells among the EPCR⁺ population enriched the sample in LT-HSCs (FIG. 8B). Importantly, CD90 expression or lack of CD45RA did not allow for a significant additional subdivision of the EPCR⁺CD34⁺ population since this subfraction is largely CD90⁺CD45RA⁻. Conversely, selection of EPCR⁺ cells from the CD34⁺CD45RA⁻ and CD34⁺CD90⁺ populations enriched these samples in LT-HSCs by approximately 8- and 3-fold respectively, indicating that EPCR expression marks a subfraction of CD34⁺/CD90⁺/CD45RA⁻ cells.

Figure 9A:
FIG. 9A is a schematic presentation for EPCR sort and transplantation strategy. CD34$^+$ cord blood (CB) cells were expanded for 3 days in UM171 (38 nM) before they were sorted on EPCR expression (EPCR$^+$ and EPCR$^{Low/-}$) where they proliferated in UM171-cultures for additional 7 days. EPCR subsets in addition to unpurified cells were stained for HSC phenotype and transplanted in NSG mice to determine their in vivo proliferative potential at the day of the sort (day 3) and after 7 day expansion (day 10).
Figure 9B:
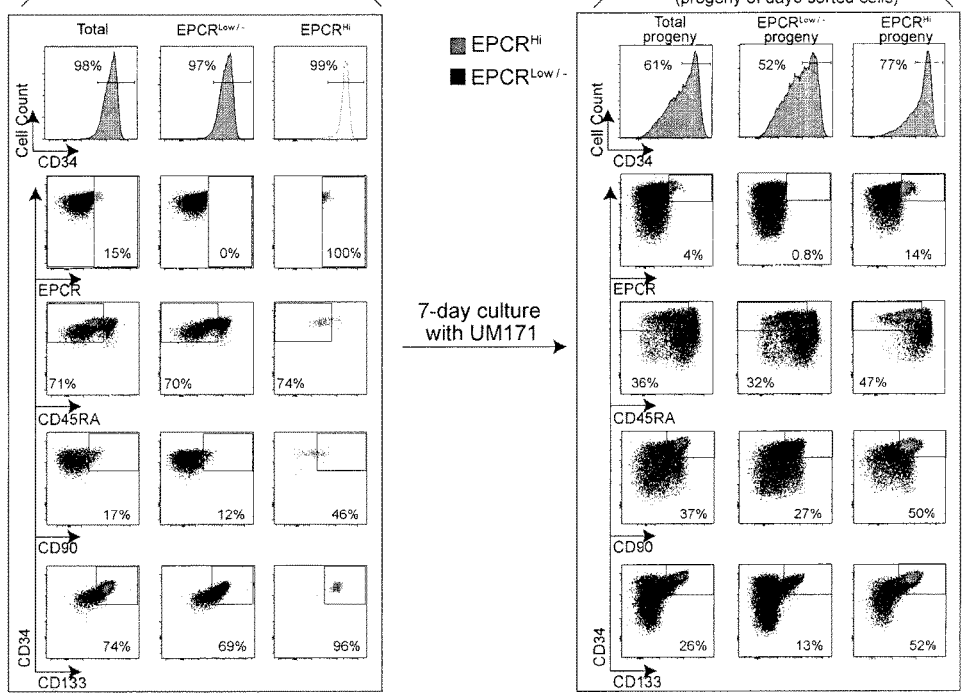
FIG. 9B is a flow cytometry of HSCP phenotype at day 3 and day 10 culture.
Figure 9D:
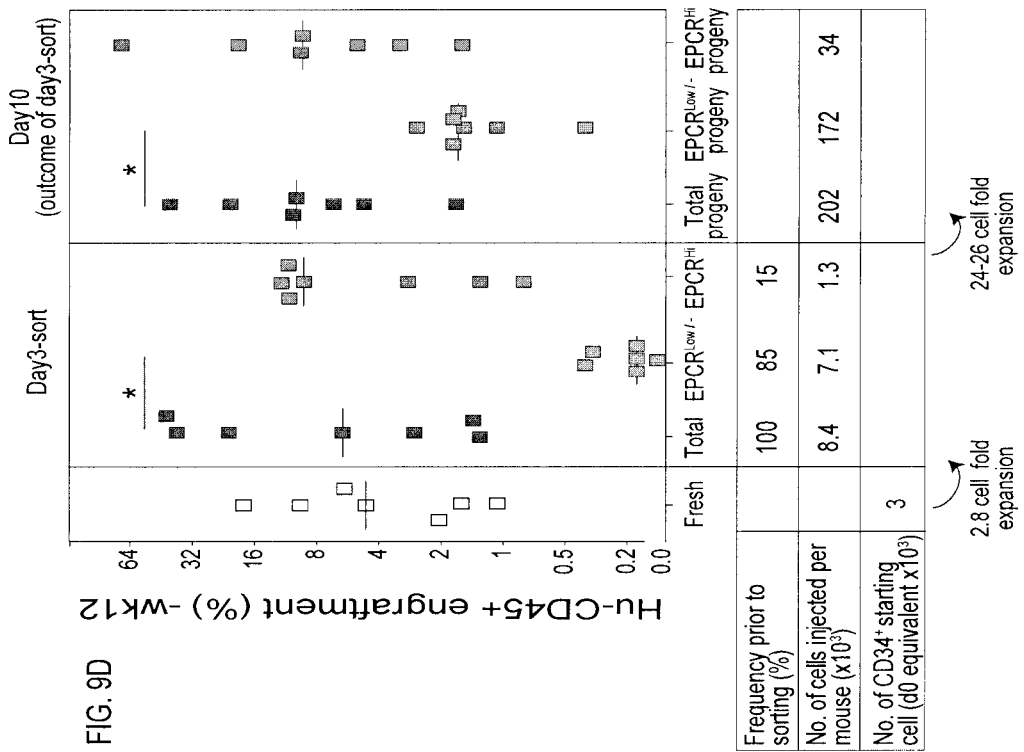
FIG. 9D illustrates the human CD45 engraftment in NSG mice receiving the indicated sorted population at day 3 or their outputs after 7-day expansion. The horizontal bars indicate median values (n=7 mice per condition, technical replicates); significance level *P<0.05 (Mann-Whitney test, one-sided).
Figure 9C:
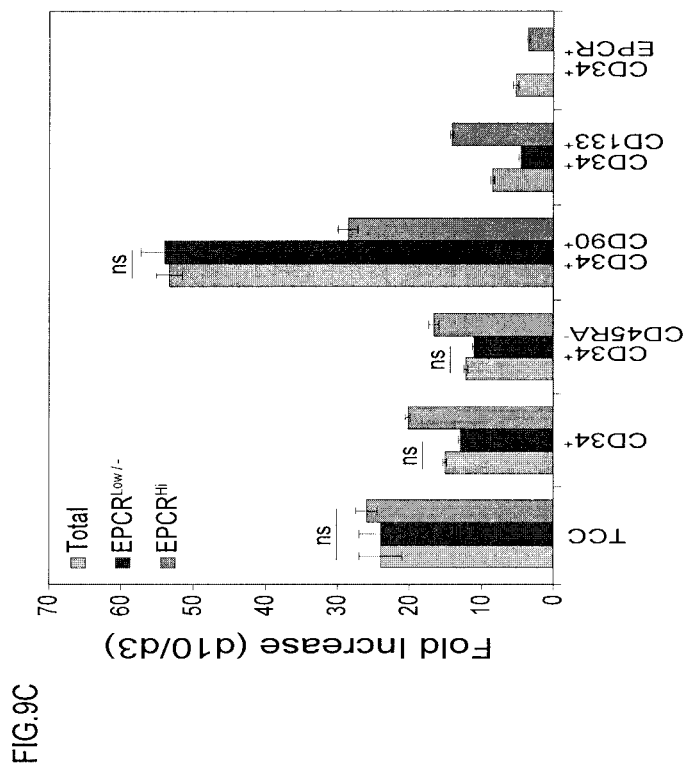
FIG. 9C shows the fold-expansion of the indicated HSPCs population from day 3 to day 10 of the expanded progenies (unpurified, EPCR$^+$ and EPCR$^{Low/-}$ cells), (mean±s.d, n=3 technical replicates. Differences between conditions are statistically significant, unless specified ns: not significant (Mann-Whitney test, one-sided).
Figure 10A:
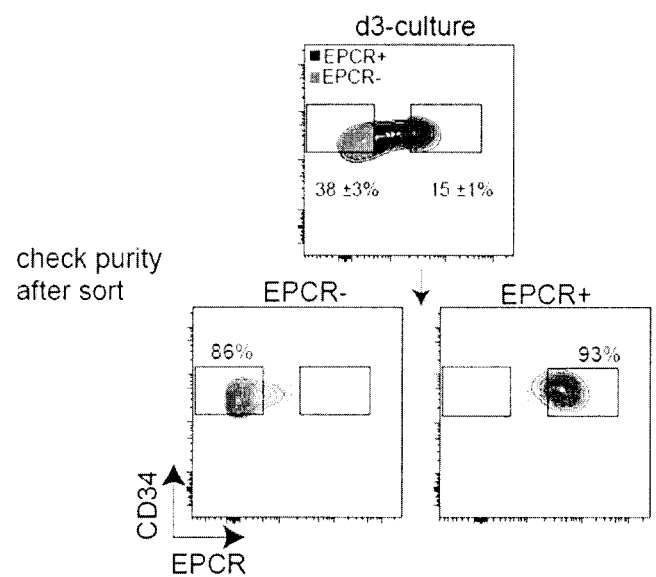
FIG. 10A is schematic presentation for EPCR sort. CD34$^+$ CD45RA$^-$ cord blood (CB) cells were expanded for 3 days in UM171 (38 nM) before they were sorted on EPCR expression (EPCR$^+$ and EPCR$^-$).
Figure 10B:
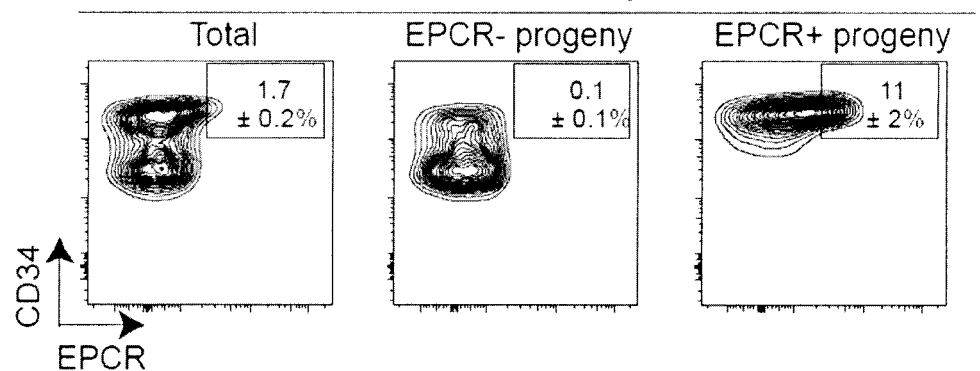
FIG. 10B shows EPCR surface expression after 7-day culture in UM171 (38 nM). Data presented as mean±s.d of 3 biological replicates.

To further evaluate the importance of EPCR expression on ex vivo expanded LT-HSCs and determine the value of additional markers such as CD133, EPCR⁺ and EPCR$^{Low/-}$ populations were sorted from CD34⁺ CB cells following a 3-day culture with UM171 and expanded them separately for an additional 7 days at which time phenotypical analyses were conducted prior to transplantation in NSG mice (FIG. 9A, 9B). Results confirm that most of the LT-HSC activity resides in the EPCR⁺ population (FIG. 9C, 9D and FIG. 10). Most interestingly, in cultures initiated with CD34⁺ EPCR$^{low/-}$ cells, it was noticed a large expansion of CD34⁺ CD90⁺ and CD34⁺CD133⁺ cells (FIG. 9C) which contributed poorly to in vivo reconstitution (FIG. 9D) once again highlighting that a subset of EPCR-negative cells which remain positive for CD34, CD90, CD133 and depleted of CD45RA expression show modest repopulation activity.

Figure 11A:
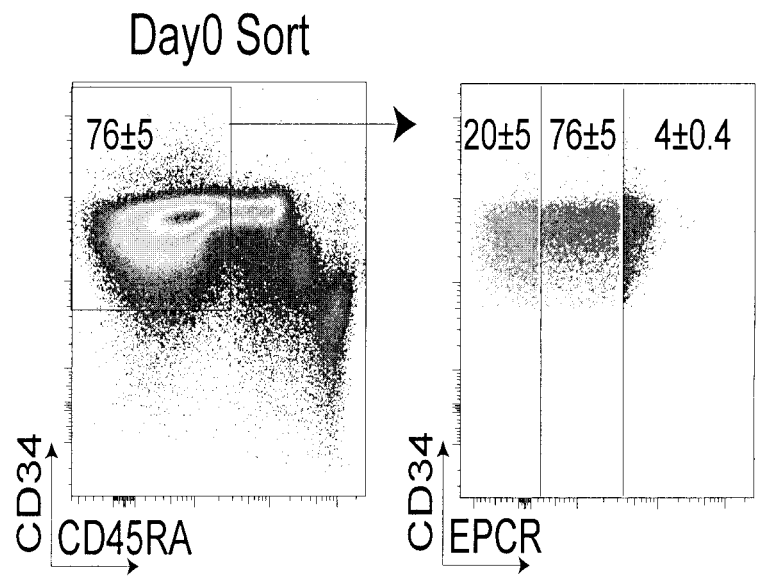
FIG. 11A is FACS representation of different EPCR subsets sorted from uncultured CD34$^+$CD45RA$^-$ cells.
Figure 11B:
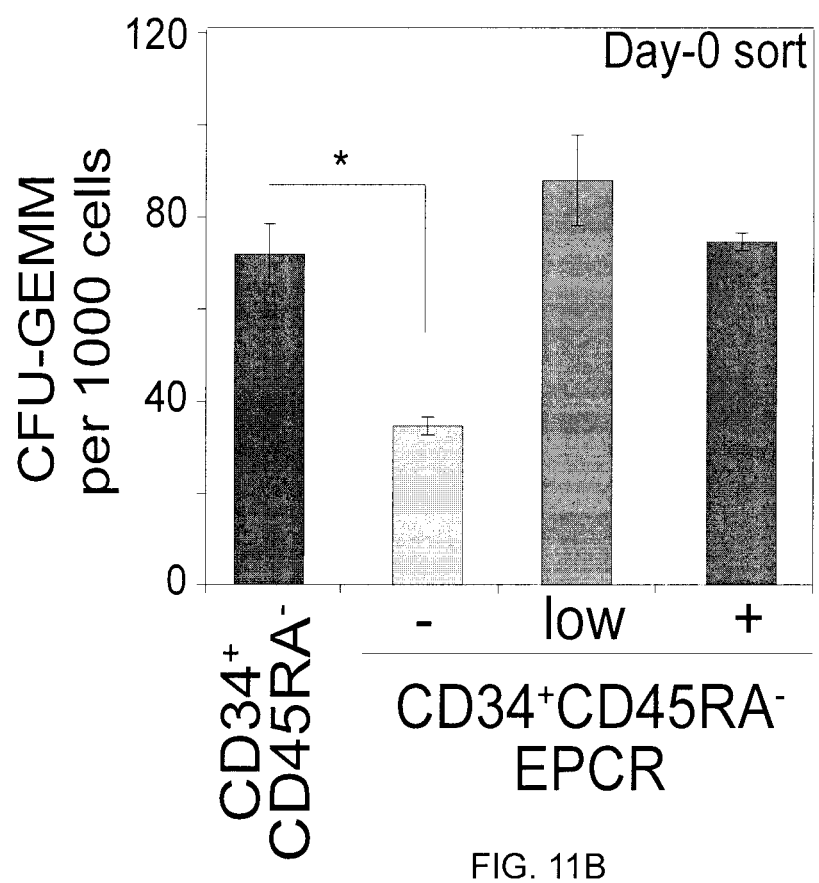
FIG. 11B shows CFU-GEMMs count per 1×10$^3$ sorted population (mean±s.d, n=3 wells counted per condition of 2 biological replicates); significance level *P<0.05 (Mann-Whitney test, one-sided).
Figure 11C:
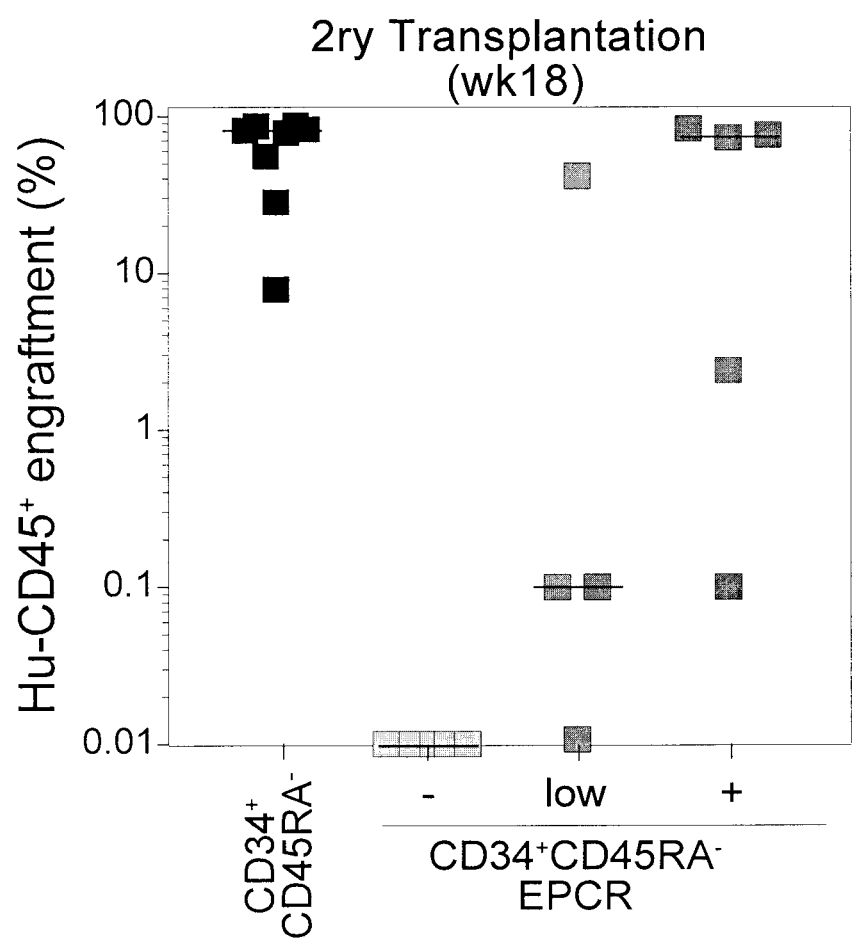
FIG. 11C show primary NSG recipients injected with uncultured indicated population were sacrificed at 24 weeks post-transplantation (n=5 mice, technical replicates). Eighty percent of the collected bone marrow cells from the 1ry NSG recipients presented in (c) were transplanted into 2ry recipients. Human (Hu) CD45 cell chimerism was analyzed in the secondary mice at 18 weeks post-transplantation by flow cytometry.

It was determined if EPCR can identify LT-HSCs from non-expanded samples (FIG. 11A). Frequencies of multilineage progenitors were similar between CD34⁺CD45RA⁻ EPCR$^{low}$, CD34⁺CD45RA⁻ EPCR⁺ and unfractionated CD34⁺CD45RA⁻ populations (FIG. 11B). It was also noticed that long-term reconstitution was mostly observed in secondary recipients of a graft originating from CD34+ CD45RA−EPCR+ cells (FIG. 11C). Based on this it appears that the EPCR⁺ subset of fresh human HSC is more primitive than the EPCR⁻ one.

Figures 12A, 12B:
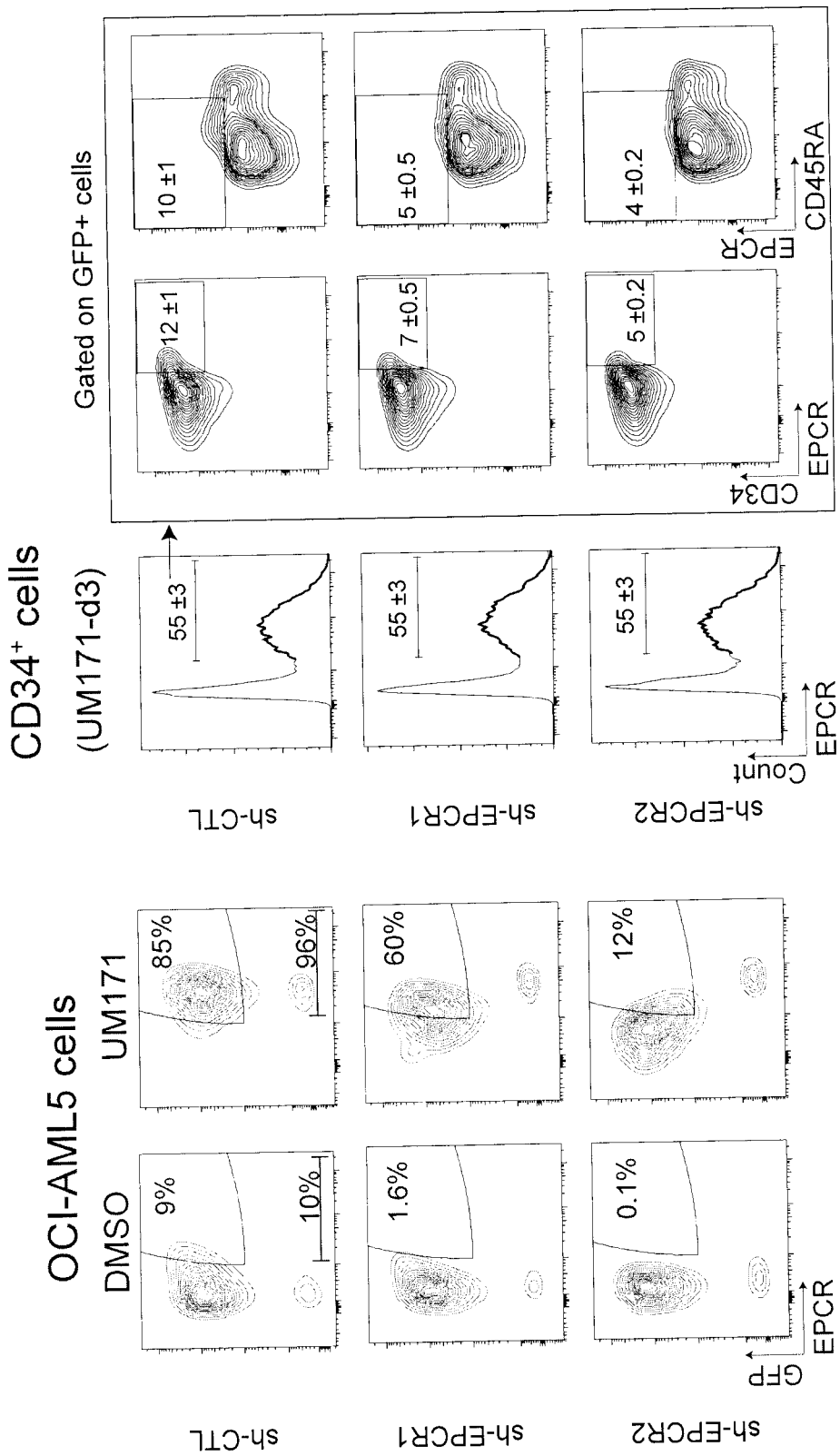
FIG. 12A shows that EPCR knockdown validation in OCI-AML5 cell line. UM171 treatment induces the EPCR surface expression up to 85% in OCI-AML5 cell line (upper panel). OCI-AML5 cells were transduced with lentiviral sh-EPCRGFP (sh1 or 2) vs controls (sh-*Renilla*) at MOI 3 for 16 hours before they washed and cultured for 2 additional days with vehicle (DMSO) or UM171 (250 nM). OCI-AML5 cells were then collected and stained for EPCR. The knockdown of EPCR was assessed in GFP$^+$ cells using flow cytometry.
FIG. 12B shows representative FACS plots of CD34$^+$ CB cells after EPCR knockdown (mean±s.d, n=3 technical replicates). Pre-stimulated CD34$^+$ CB cells were infected with lentiviral sh-EPCR-GFP (sh1 or 2) vs controls (sh-*Renilla*) at MOI 100 for 16 hours. Transduced CD34$^+$ CB cells were washed and cultured with or without UM171 (38 nM) for 3 days where the knockdown of EPCR surface expression in GFP$^+$ cells was monitored using flow cytometry. Cells then were kept in culture for total of 7 days before they were injected in NSG mice to monitor their in vivo activity.
Figure 12C:
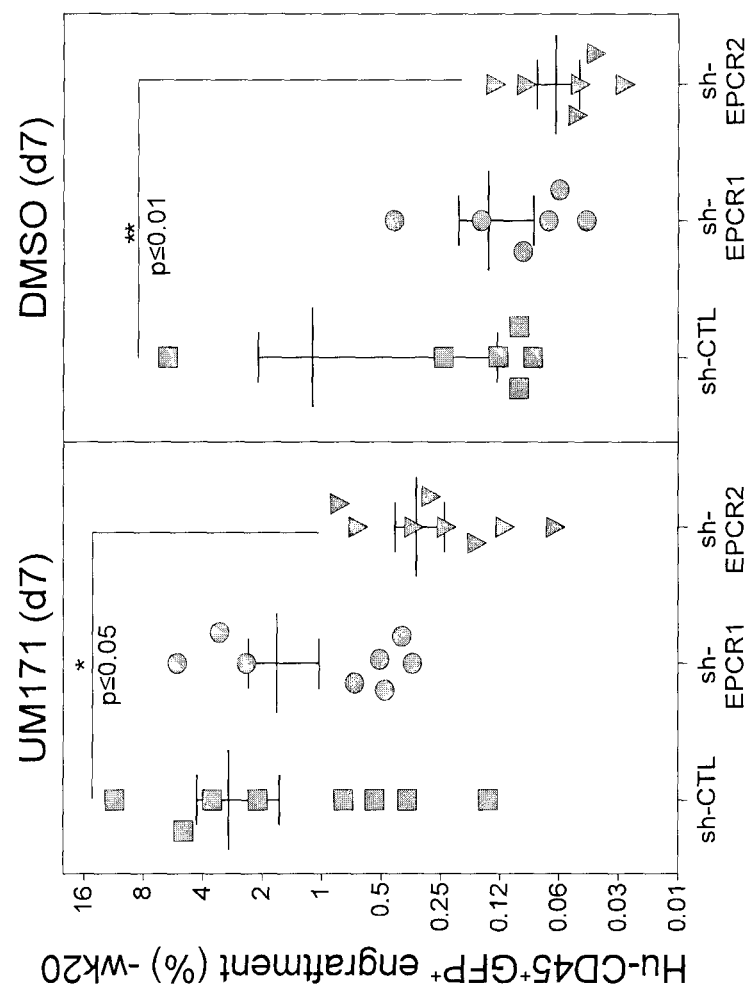
FIG. 12C illustrates human (Hu)-CD45 engraftment in GFP+ populations in bone marrow of NSG at 20 weeks post-transplantation (mean with s.e.m, n=4-5 mice per condition, technical replicates). Two different sh-EPCR are shown; significance level *P<0.5 (Mann-Whitney test, one-sided).
Figure 13A:
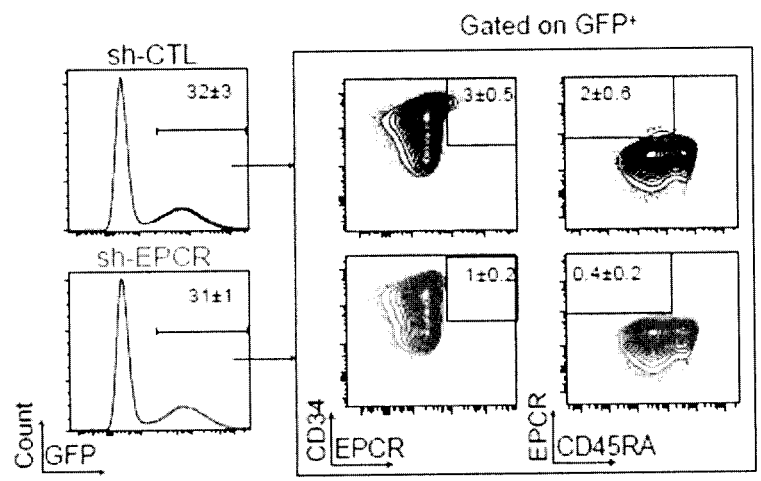
FIG. 13A shows pre-stimulated CD34$^+$ CB cells were infected with lentiviral sh-EPCR-GFP (sh1 or 2) vs controls (sh-*Renilla*) at MOI 100 for 16 hours. Transduced cells were washed and expanded in the presence of UM171 (38 nM) for a total of 8 day-culture. FACS analysis was then performed to assess the EPCR knockdown in GFP$^+$ cells (mean±s.d, n=3 technical replicates).
Figure 13B:
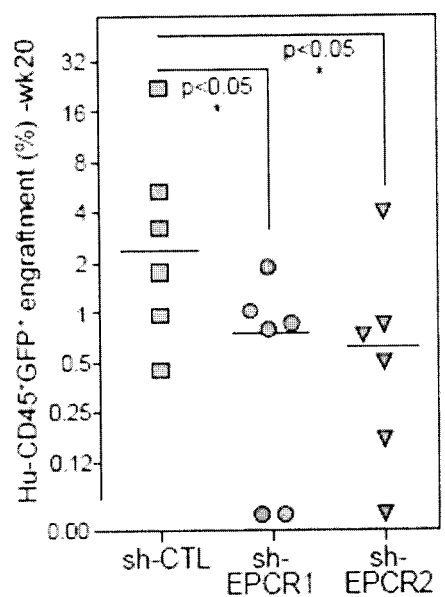
FIG. 13B illustrates human (Hu)-CD45 engraftment in GFP+ populations in bone marrow of NSG at 20 weeks post-transplantation (n=4-5 mice per condition, technical replicates). Two different sh-EPCR are shown. The horizontal bars indicate median values, significance level *P<0.5 (Mann-Whitney test, one-sided).

To determine if EPCR expression is essential for HSPC activity, 2 effective EPCR-targeting shRNA vectors were identified which enabled different levels of knockdown (FIGS. 12A and 12B). CD34⁺ CB cells transduced with the indicated shEPCR-GFP vectors were transplanted into NSG mice whose reconstitution by human cells was analyzed 20 weeks post-transplantation (FIG. 12C and FIG. 13). Results show that HSPC activity is inversely proportional to the magnitude of EPCR knockdown—the most efficient shEPCR (sh2) significantly reduces the engraftment levels. These results indicate that EPCR levels are critical for the in vivo activity of human HSPCs.

Figure 14A:
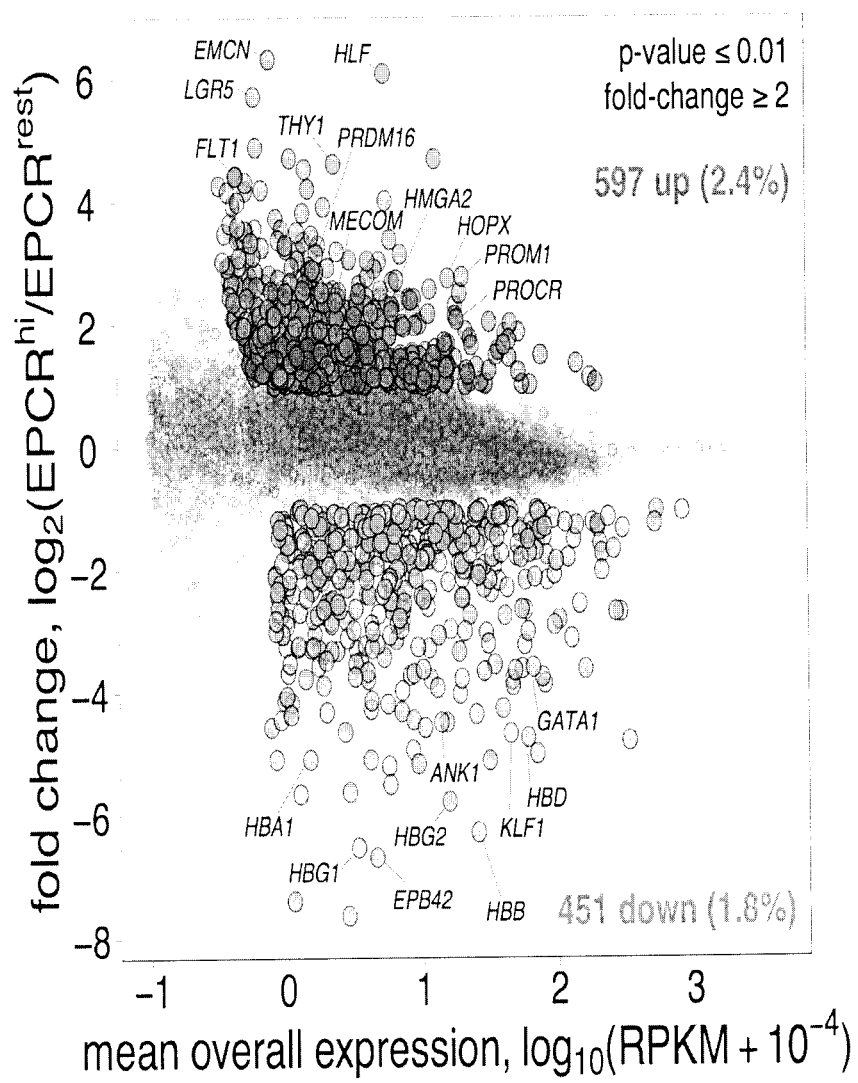
FIG. 14A shows scatter plot representation of global mRNA profiling showing upregulated (red) and down-regulated (blue) genes in EPCR$^+$ versus EPCR$^{Rest}$ (− and low) populations (p≤0.01, mean expression ≥1 RPKM; ≥2-fold up or down).
Figure 14B:
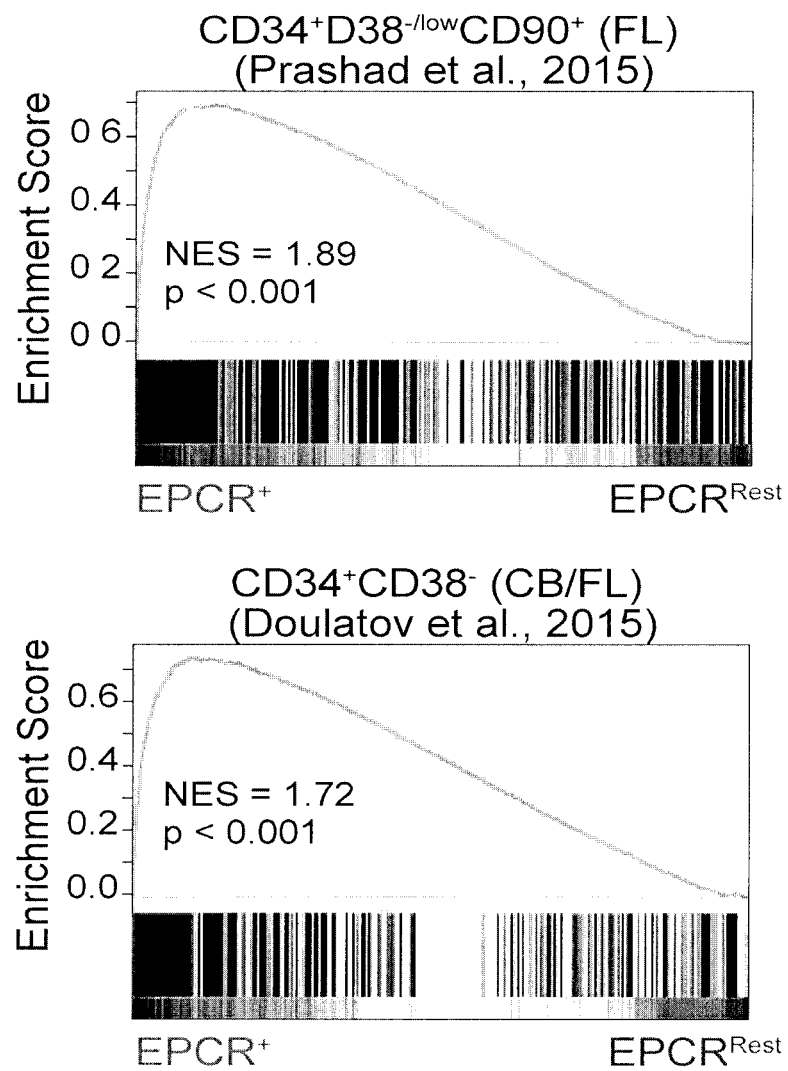
FIG. 14B illustrates GSEA plot showing enrichment for HSC-related genes in the EPCR$^+$ population. Gene expression of uncultured purified human HSC derived from cord blood (CB) and fetal liver (FL) from two independent data set were used for the GSEA analysis; NES=normalized enrichment score; all comparisons were significant.
Figure 14C:
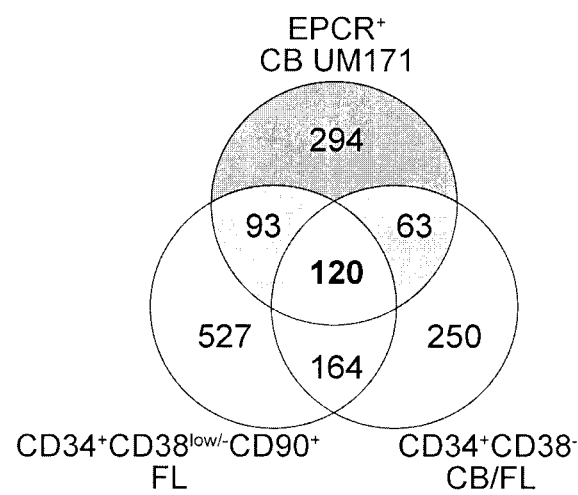
FIG. 14C is a Venn diagram plot showing the number of common and distinct up-regulated genes in EPCR$^+$ population, CD34+CD38low/−CD90+ (FL) cells, and CD34+CD38− (FL and CB) cells. mRNA (FIG. 14D) and protein (FIG. 14E) levels of known HSC surface markers in various cellular population.
Figure 14D:
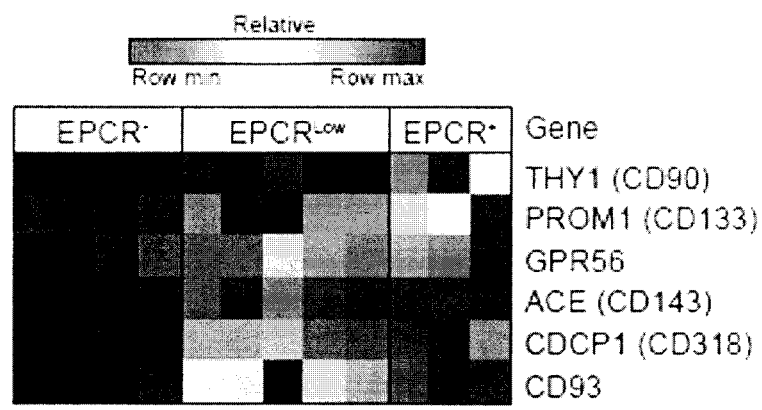
FIG. 14 illustrates that gene expression profiling of cultured EPCR$^+$ population strongly correlates with uncultured HSC-related genes.
Figure 14E:
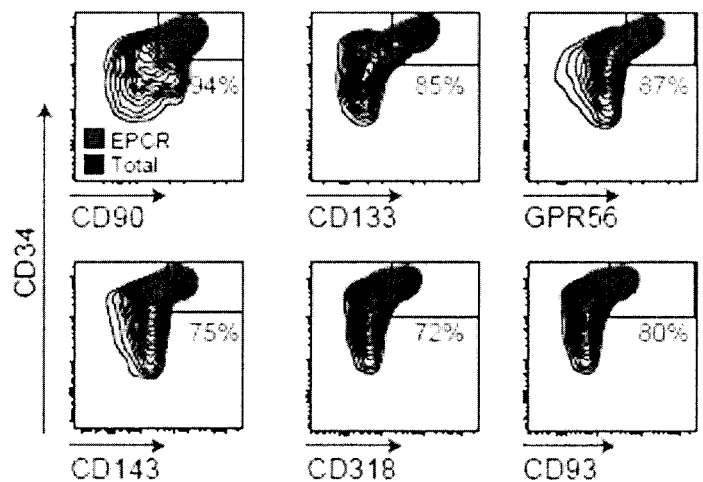
Figure 15A:
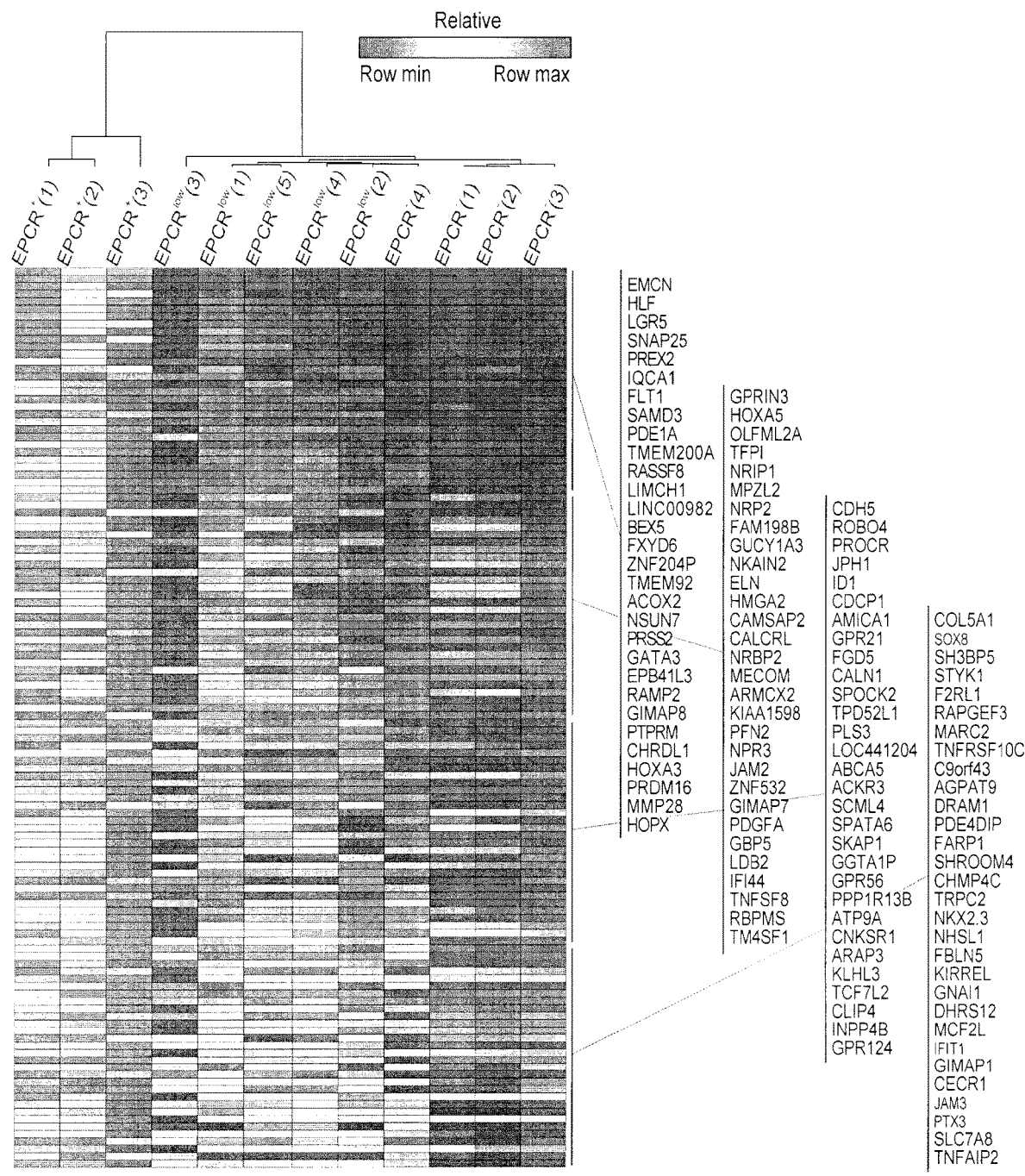
FIG. 15A is a heat map showing relative expression patterns of 120 common up-regulated genes in EPCR$^+$ population, CD34$^+$CD38$^{low/-}$CD90$^+$ fetal liver (FL) cells, and CD34$^+$CD38$^-$ FL and cord blood cells.
Figure 15B:
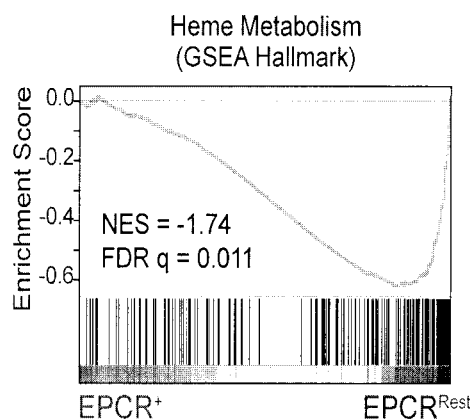
FIGS. 15B and 15C are GSEA plot shows downregulation of (FIG. 15B) hemoglobin levels and (FIG. 15C) progenitor genes in EPCR+ cells.
Figure 15C:
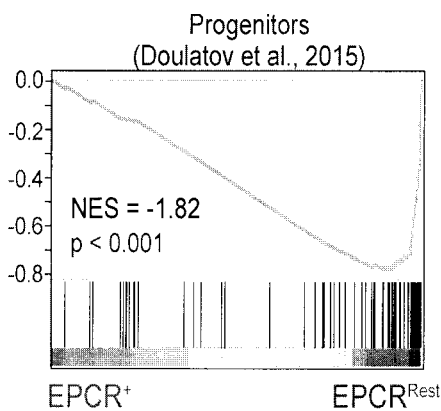
Figure 15D:
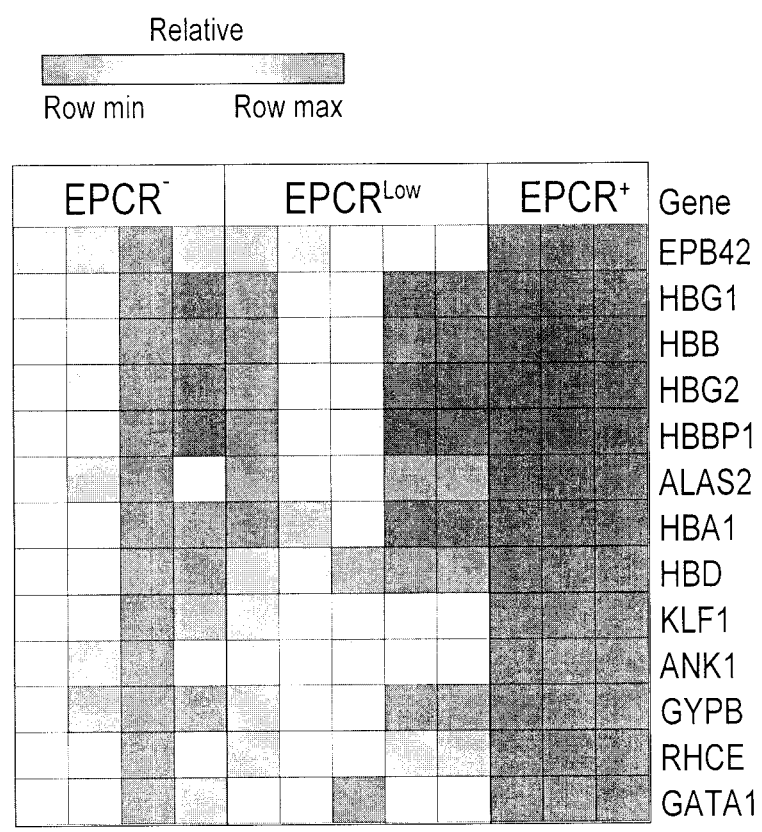
FIG. 15D is a heat map showing marked suppression of transcripts associated with erythroid development/differentiation in EPCR+ cells.

In order to analyze the transcriptional landscape of EPCR⁺ cells, mRNA profiling experiments were performed using EPCR⁻, EPCR$^{low}$ and EPCR⁺ populations sorted from expanded CD34⁺CD45RA⁻ CB cells (FIG. 3B, day 7). Using a minimum of 2-fold difference in expression as a selection criterion, a total of 1,048 differentially expressed genes (597 up- and 451 down-regulated genes) were identified between the EPCR⁺ and EPCR$^{-/low}$ populations (FIG. 14A). Gene set enrichment analysis (GSEA) shows that the differentially expressed genes of EPCR⁺ population are significantly overlapped with genes associated with HSPC derived from uncultured human CB and fetal liver, providing evidence for a stem cell signature (FIG. 14B and FIG. 15). Manual curation and GSEA identified a marked underrepresentation of differentiation-related genes in the EPCR⁺ population, namely genes associated with erythroid and myeloid differentiation (FIG. 14A and FIG. 15B and FIG. 15C). A 120 HSPC gene signature was identified (FIG. 14C and FIG. 15A). This signature is mostly comprised of either well-known transcriptional regulators of HSC self-renewal/ function such as HLF, PRDM16, and MECOM or genes encoding cell surface markers typically used to enrich for HSC (CD90, CD133, CD143, CD318, CD93 and GPR56) (FIGS. 14A and 14D). It was further validated the overlapping expression patterns of these cell surface markers with that of EPCR by flow cytometry (FIG. 14E).

It is thus disclosed that EPCR represents a new robust marker of expanded human LT-HSCs. Accordingly; expanded human LT-HSPCs can be defined by the expression of a single gene product rather than group of receptors. Indeed in UM171-supplemented culture conditions, EPCR cell surface expression on its own identifies functional HSPC at a frequency which cannot be further improved by any of the previously defined cell surface markers such as CD34, CD90, CD49f or CD133.

EPCR-positive cells are approximately 3 to 4 times more frequent at day 7 than at day 12 of the culture. Thus, HSC activity measured in expanded cultures was >4 times greater when CB cells were expanded for 7 days compared to 12 days. Accordingly, EPCR monitoring also represents a new method to predict expansion levels of human CB-derived HSPCs.

EPCR-positive HSCs are competent for both short-term (3 weeks) and long-term (24 weeks) reconstitution, therefore distinguishing cells with LT from cells with ST repopulation potential within the EPCR$^+$ subset is the next step for future investigation.

ShRNA-mediated EPCR knockdown studies show that EPCR plays a crucial role for the in vivo activity of HSPCs. Interestingly, mice genetically engineered to express low levels of EPCR (Procr$^{low}$) showed defects in HSPC bone marrow retention and limited long-term reconstitution potential, strengthening the idea that EPCR is an important regulator of HSPC.

Transcriptional profiling of EPCR$^{-/low}$ and EPCR$^+$ populations sorted from expanded CB shows striking molecular differences between these populations, with the genetic makeup governing HSC specification and function being reflected in the EPCR$^+$ fraction.

Encompassed herein are the starting population of cell culture being stimulated with at least one cell expanding factor as known in the art. For example, UM171, UM729, or analogs thereof, lenalidomide and/or thalidomide. Alternatively, the selected or filtered population of cells, such as for example CD34$^+$ and/or EPCR$^+$ cell population, can be also stimulated with UM171, UM729, or analogs thereof, lenalidomide and/or thalidomide Accordingly, the expanding factor can be:

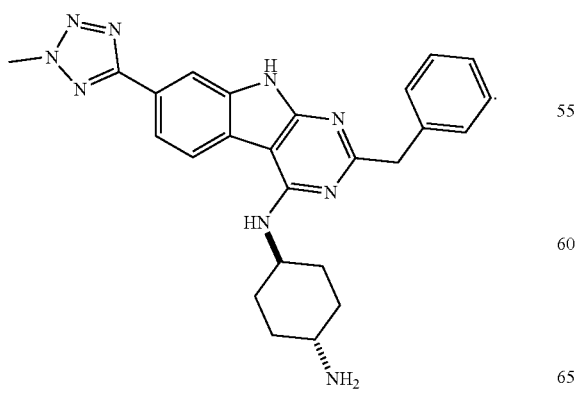

UM171

In another embodiment, the expending factor can be:

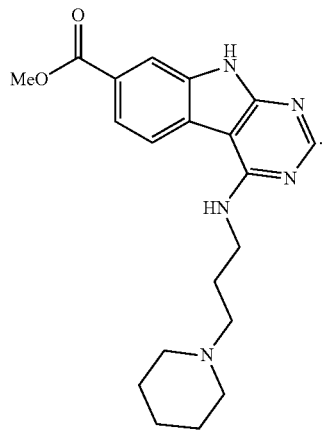

(UM729)

Alternatively, the expanding factor is an analog having the following structure:

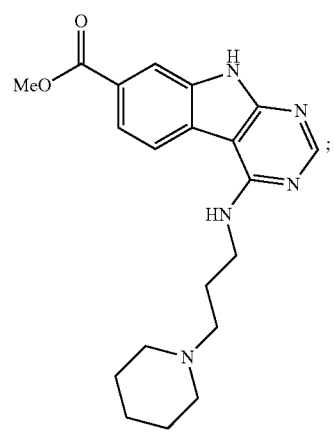

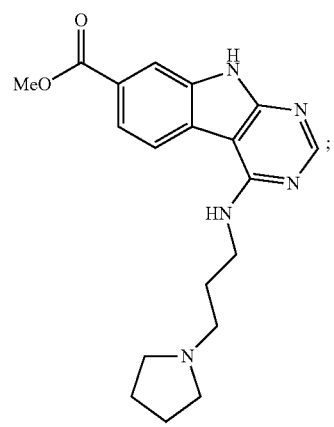

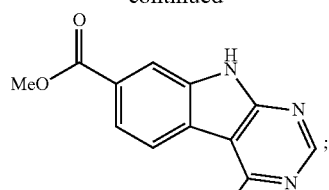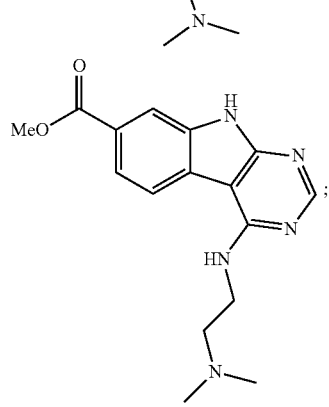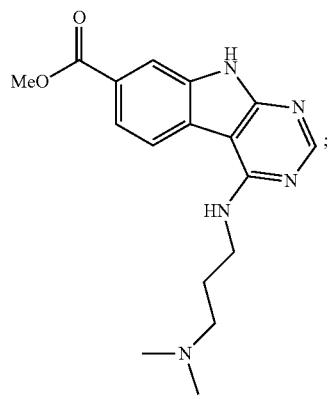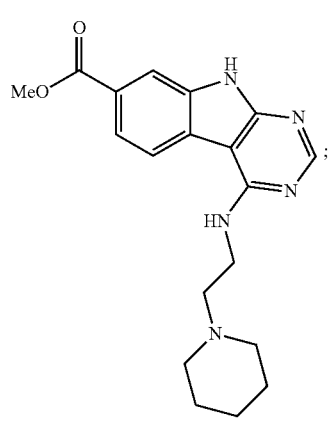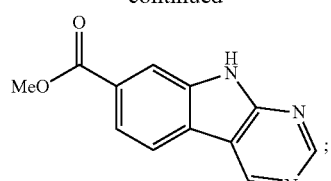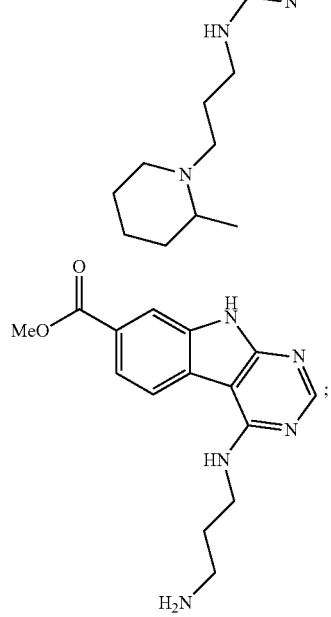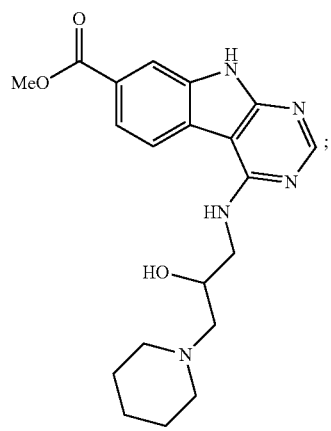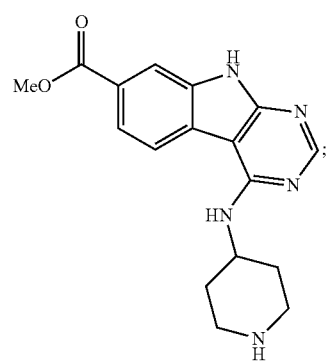

-continued
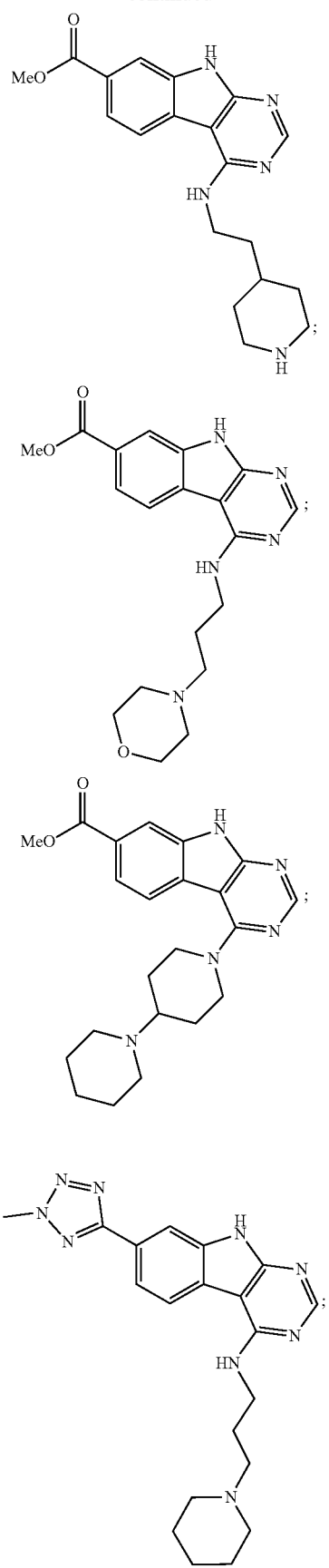
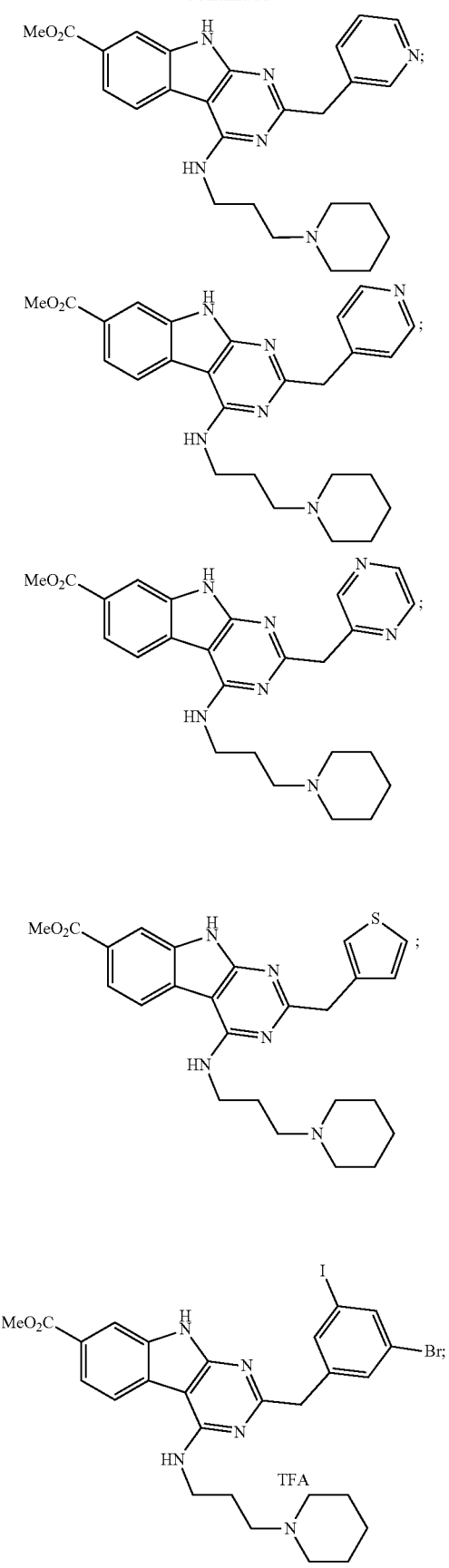

-continued
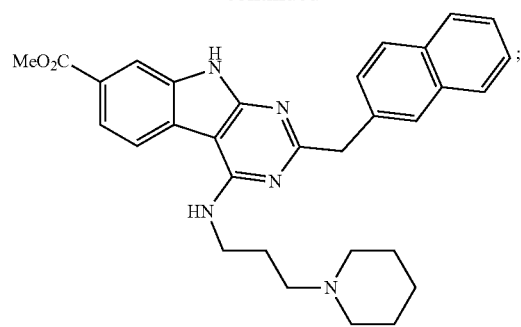
TFA
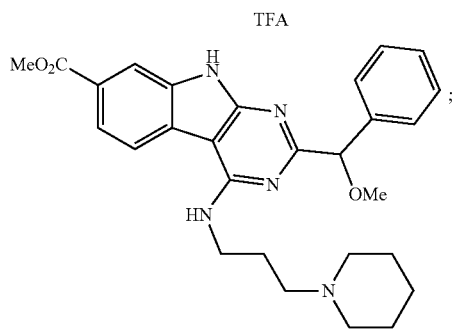
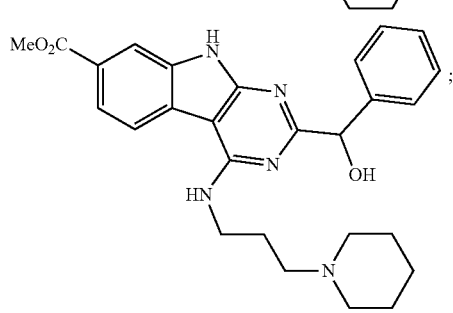
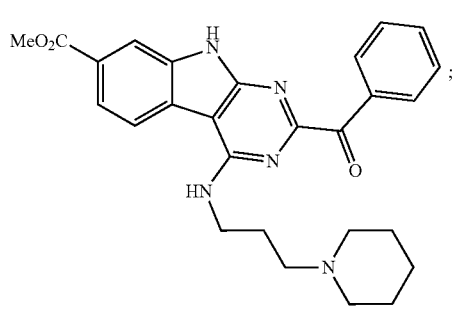
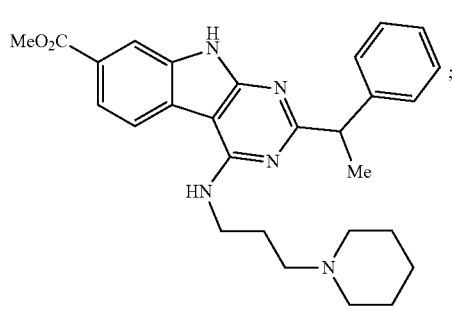
-continued
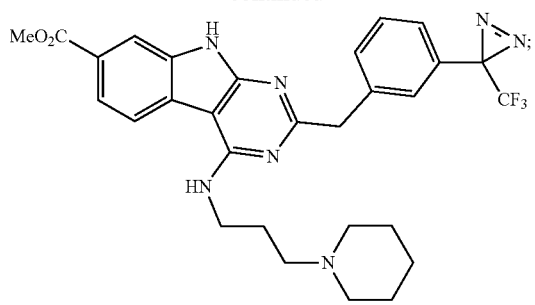
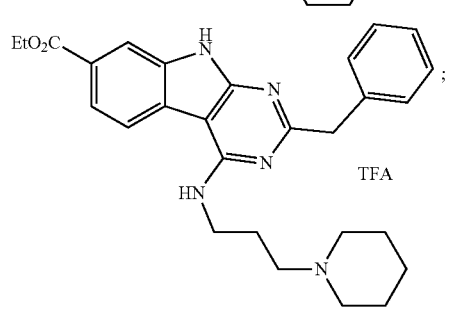
TFA
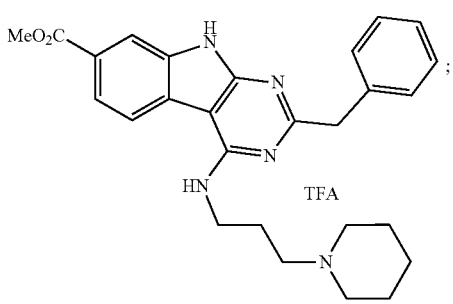
TFA
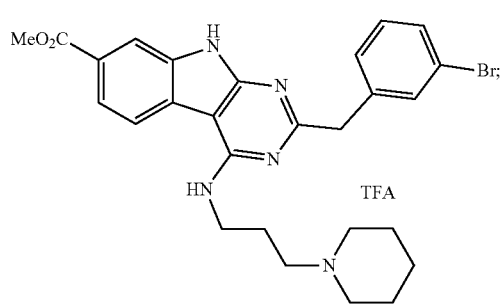
TFA
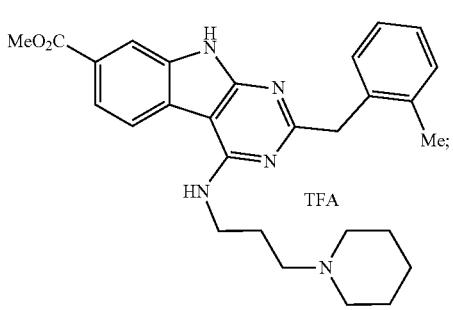
TFA -continued
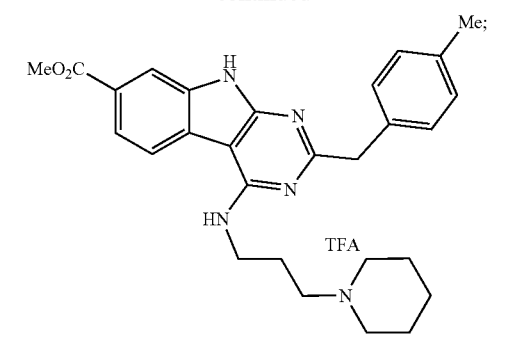
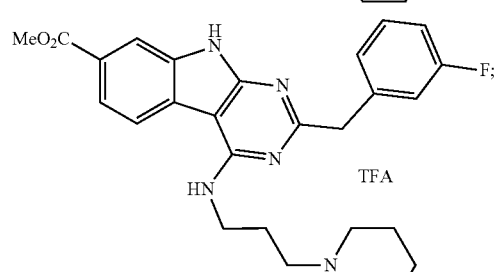
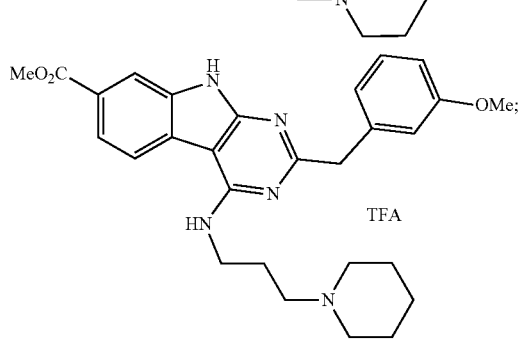
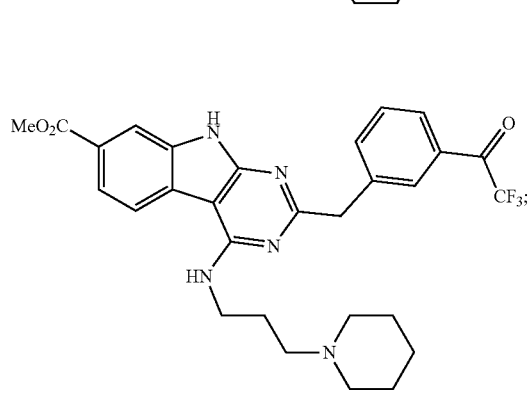
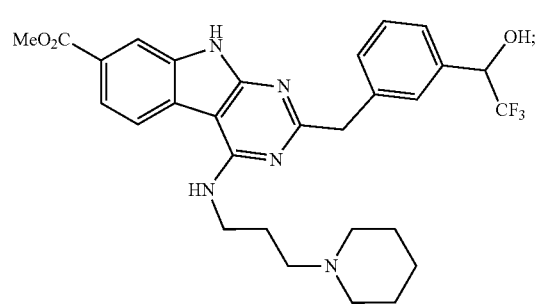
-continued
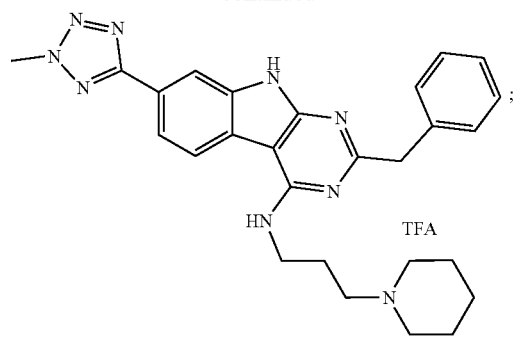
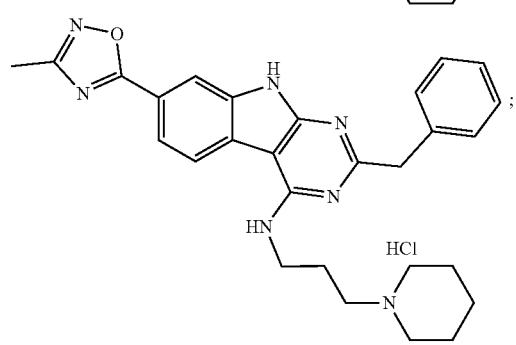
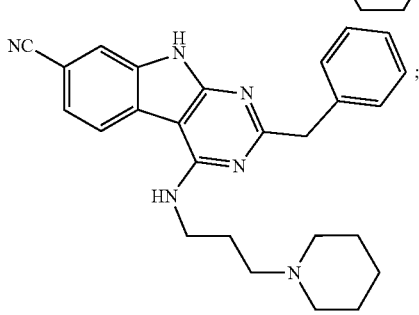
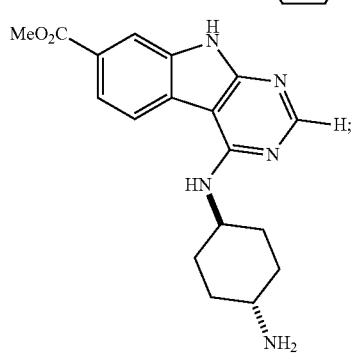
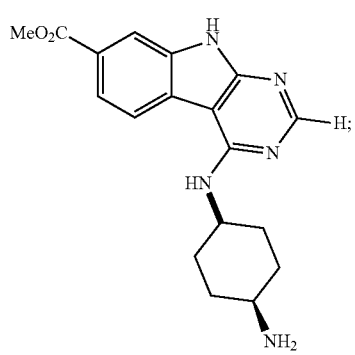

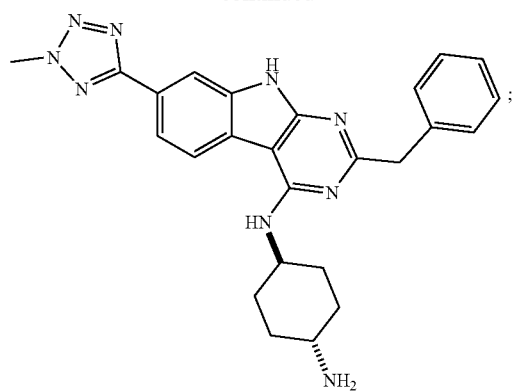
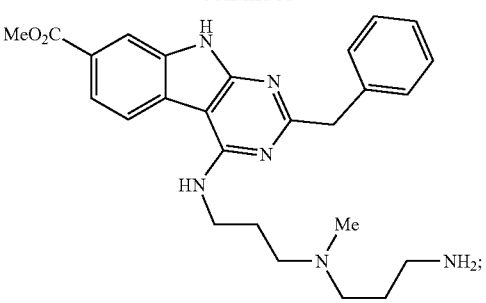
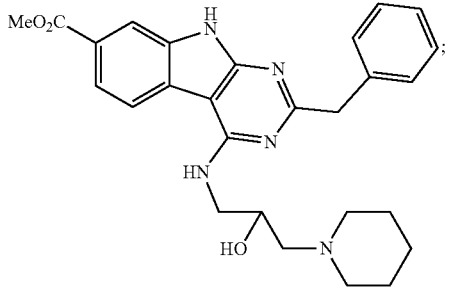
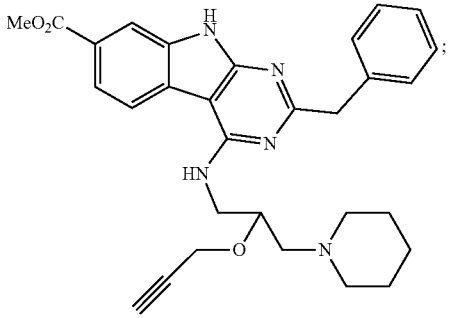
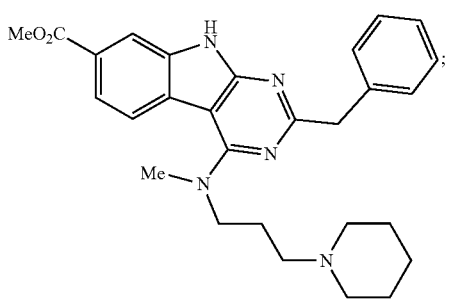
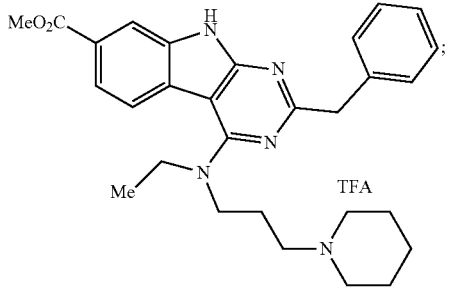

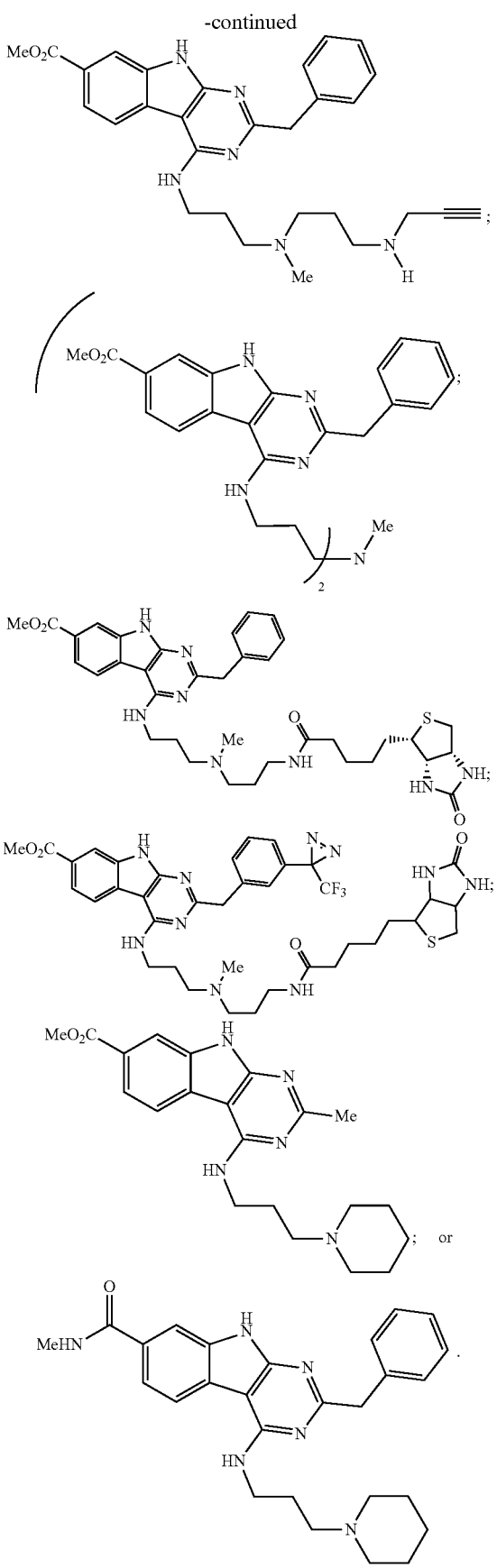

Figure 17:
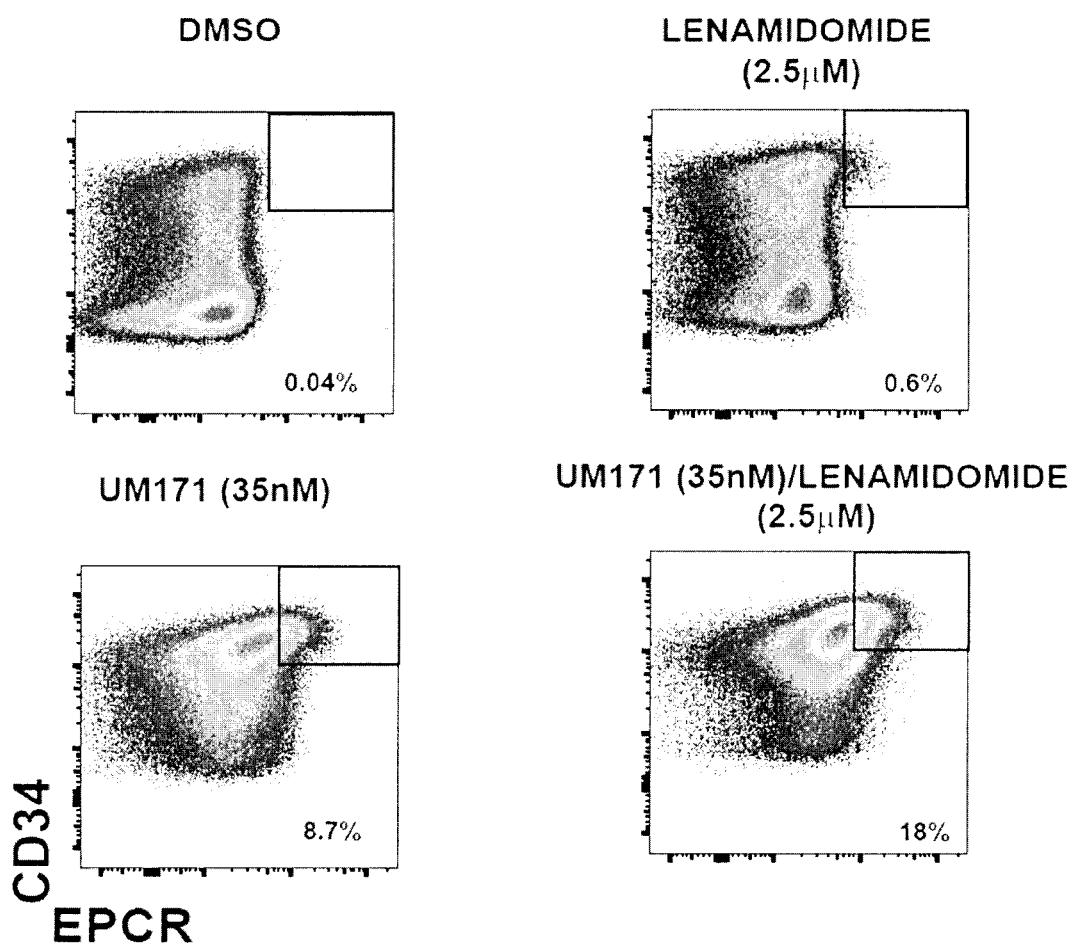
FIG. 17 illustrates CD34+ cells expanded with lenamidomide alone or in combination with UM171 enriches EPCR+ population of cells.

As seen in FIG. 17, a combination of UM171 and lenalidomide is effective in stimulating EPCR+ cells expansion. Also encompassed is further in combination, the use of an aryl hydrocarbon receptor antagonist such as for example, but not limited to, Stem Regenin 1 (SR1) with a cell expanding factor as described herein in order to stimulate EPCR$^+$ cell expansion. In an embodiment, at least one cell expanding factor can be used to stimulate a starting population of cells before the filtering, such as for example UM171 UM729, lenalidomide and/or thalidomide and/or in combination SR1 as described herein.

The EPCR+ cells described herein can also be expanded in a bioreactor as per known techniques in the art.

Furthermore, in addition in selecting EPCR$^+$ cells, the targeted stem cells for expansion can also be enriched prior or after the selection of the EPCR$^+$ cells by harvesting CD34$^+$, CD38$^+$, CD90$^+$, CD45RA$^+$, CD133 and/or CD49f$^+$ cells, such as for example as described hereinabove, to obtain CD34$^+$CD45RA$^-$ cells prior in selecting EPCR$^+$ cells.

Accordingly, the population of Endothelial Protein C Receptor (EPCR)$^+$ cells expanded by the method described herein can be used for stem cells transplantation in a recipient, such as for example in recipient is a human patient or an animal (e.g. mouse).

Also encompassed herein is the use of EPCR$^+$ cells expanded by the method described herein for treating a hematopoietic disorder/malignancy, an autoimmune disease and/or an inherited immunodeficient disease in a subject.

It is further encompassed the use of EPCR$^+$ cells expanded by the method described herein for treating a subject in need of a treatment with cell gene therapy. As described in WO2016/041080, the content of which is incorporated herein by reference, encompassed herein is a method of treating a subject in need of a treatment with cell gene therapy, the method comprising administering to the subject an effective amount of a population of EPCR$^+$ transduced cells. Accordingly, it is encompassed a method for expressing a gene of interest in a cell, said method comprising transducing EPCR$^+$ cells with a viral vector comprising a nucleic acid encoding a gene of interest.

Essentially, a viral vector is transduced into EPCR$^+$ cells thereby obtaining a population comprising transduced cells; and (ii) administering to a subject an effective amount of the population comprising transduced cells.

The term "viral vector" as used herein refers to a recombinant virus capable of transducing cells and introducing their genetic material into the cells. Examples of viral vectors that may be used in gene therapy include retroviruses (lentiviruses), adenoviruses, adeno-associated viruses, herpesviruses (herpes simplex viruses), alphaviruses, and vaccinia viruses (Poxviruses). In an embodiment, the viral vector is a lentiviral vector.

The term "lentiviral vector" refers to a vector containing structural and functional genetic elements outside the LTRs that are primarily derived from a lentivirus. Lentiviral vectors are capable of providing efficient delivery, integration and long term expression of transgenes into non-dividing cells both in vitro and in vivo. In another aspect, it is provided a method for transiently expressing a gene of interest into EPCR$^+$ cells, said method comprising transducing said EPCR$^+$ cells with a non-integrating viral vector comprising a nucleic acid encoding a gene of interest.

As used herein, the term "transduction" refers to the stable transfer of genetic material from a viral particle (e.g., lentiviral) to a cell genome (e.g., primitive hematopoietic cell genome). It also encompasses the introduction of non-integrating viral vectors into cells, which leads to the transient or episomal expression of a gene of interest present in the viral vector. Viruses may be used to infect cells in vivo, ex vivo, or in vitro using techniques well known in the art. For example, when cells, for instance EPCR$^+$ cells are transduced ex vivo, the vector particles may be incubated with the cells using a dose generally in the order of between 1 to 100 or 1 to 50 multiplicities of infection (MOI) which also corresponds to $1\times10^5$ to 100 or $50\times10^5$ transducing units of the viral vector per $10^5$ cells. This, of course, includes amount of vector corresponding to 1, 2, 3, 4, 5, 6, 7, 8, 9, 10, 15, 20, 25, 30, 35, 40, 45, and 50 MOI.

Prior to, during, and/or following transduction, the cells may be cultured in media suitable for the maintenance, growth, or proliferation of the cells.

Particularly, the hematopoietic disorder/malignancy, the autoimmune disease and/or the inherited immunodeficient disease comprise bone marrow failure conditions, lupus, acute myeloid leukemia, acute lymphoblastic leukemia, chronic myeloid leukemia, chronic lymphocytic leukemia, myeloproliferative disorders, myelodysplastic syndromes, multiple myeloma, non-Hodgkin's lymphoma, Hodgkin's disease, aplastic anemia, pure red cell aplasia, hemoglobinuria, Fanconi anemia, thalassemia, sickle cell anemia, Wiskott-Aidrich syndrome, or inborn errors of metabolism.

A method of filtering stem and progenitor cells in order to select EPCR+ cells is also described herein. The use of a filtering system, consisting of a column or beads coated with an antibody specifically binding an epitope of EPCR is encompassed herein. Example of such systems, but not limited to, are Clinimacs®, or cell separation platforms from STEMCELL Technologies (EasySep™, RoboSep™, RosetteSep™, StemSep™). Accordingly, instead of using a column as known in the art, magnetic particles (beads) can be used to filtered cells and select a population of EPCR$^+$ cells.

Any immunoprecipitation or immunodepletion method known in the art can be used to select EPCR$^+$ cells since they use an antibody that in the present case will be specific for EPCR. For example, cross-linking antibodies specifically binding an epitope of EPCR to beads or column surfaces and incubation of eluted cells with the beads or application of a cell suspension to such column and, if desired subsequent elution of the cells from the column or the beads, therefrom allows filtering and selecting from the starting population of cells EPCR$^+$ cells. The starting population of cells can be stem and/or progenitor cells, such as human hematopoietic stem cells (HSC). Preferably, the starting population of cells are fresh cells. Alternatively, the starting population can also be cultured cells.

Figure 16:
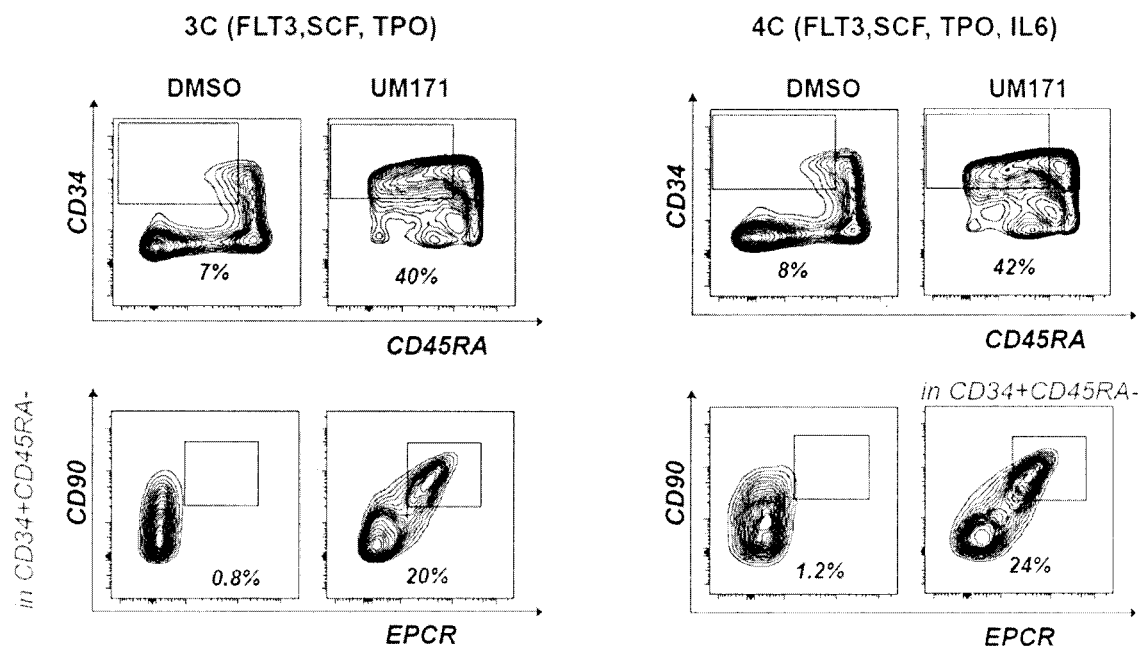
FIG. 16 illustrates that the use of a standard mix of three cytokines (FLT3, SCF and TPO) or four cytokines (FLT3, SCF, TPO and IL6) are effective in stimulating EPCR$^+$ cells expansion from CD34+ cells exposed to UM171 for days.

In an embodiment, in particular, using a starting cell population from umbilical cord blood cells, the culturing conditions comprise the use of other cell expanding factors like cytokines and growth factors, generally known in the art for HSC/HPC expansion. Such cytokines and growth factors can be biologics or small molecules and they include without limitation IL-1, IL-3, IL-6, IL-11, G-CSF, GM-CSF, SCF, FLT3 thrombopoietin (TPO), erythropoietin, and analogs thereof. As seen in FIG. 16, a combination of three cytokines (FLT3, SCF and TPO) or even four cytokines (FLT3, SCF, TPO and IL6) can be used in the culture media to expand EPCR cells as described herein. As used herein, "analogs" include any structural variants of the cytokines and growth factors having the biological activity as the naturally occurring forms, including without limitation, variants with enhanced or decreased biological activity when compared to the naturally occurring forms or cytokine receptor agonists such as an agonist antibody against the TPO receptor (for example, VB22B sc(Fv)$_2$ as detailed in patent publication WO 2007/145227, and the like). Cytokine and growth factor combinations are chosen to expand HSC and progenitor cells while limiting the production of terminally differentiated cells. In one specific embodiment, one or more cytokines and growth factors are selected from the group consisting of SCF, FLT-3, IL6, TPO, and a combination thereof.

The filtering method described herein which results in an enrichment in EPCR+ cells has been demonstrated to minimize the culturing medium that needs to be used, increases proliferation of hematopoietic stem cells and provides a mean to increase efficacy of engraftment and secondary engraftment.

The present disclosure will be more readily understood by referring to the following examples.

Example I

Human CD34$^+$ Cord Blood Cell Collection and Culture

Umbilical cord blood units were collected form consenting mothers according to ethically approved protocol at CHU Sainte-Justine, Montreal, QC, Canada. Human CD34$^+$ cord blood (CB) cells were isolated using The EasySep™ positive selection kit (StemCell Technologies Cat #18056). Sorting for more primitive phenotypes was done in additional step using BD Aria II sorter.

Fresh or cultured CB cells were labelled or sorted for different HSPC phenotypes using the following antibodies. Mouse anti-human antibodies were used to detect CD34 (FITC—BD Biosciences Cat #555821 or BV421—BD Biosciences Cat #562577), CD45RA (PE—BD Biosciences Cat #555489 or APC-cy7 BioLegend Cat #304128), CD90 (PECY7—BioLegend Cat #328124), CD49f (PECY5-BD Biosciences Cat #551129 or BV241 BioLegend Cat #313624), CD38 (PerCP-eFluor710 Myltenyi Cat #46038842), CD133 (PE Miltenyi Cat #130-080-801) and c-Kit (APC-CY7 Biolegend Cat #313228). EPCR-APC-Vio770 (clone REA337) and its corresponding isotype (clone REA293) were purchased from Miltenyi Biotech. EPCR-APC (clone RCR-401) and its corresponding isotype (clone RTK2071) were purchased from Biolegend. Cells were analyzed on a BD Canto flow cytometer, and cell sorting (under low pressure conditions) was conducted on a BD Aria II cell sorter. Cell recovery after sorting as well as purity of sorted populations were systematically evaluated after the sort for every experiment. Accordingly, cells were counted manually with a hemocytometer, and assessed for viability using trypan blue. The recovery was generally 50-60% of cell numbers estimated with the FACSAria apparatus. Purity of the sorted populations was always monitored by re-running a small fraction of the sorted populations into FACSAria; purity greater than 95% had to be achieved to proceed with the samples. For every experiment, we cultured the same number of sorted cells (according to the manual count) in the presence or absence of UM171, and monitored the fold expansion resulting from UM171 treatment following 1, 7 or 12 days of culture.

Human CB-derived CD34$^+$ or CD34$^+$CD45RA$^-$ cells were cultured in HSC expansion media consisting of StemSpan SFEM (StemCell Technologies Cat #09650) supplemented with human 100 ng/ml stem cell factor (SCF, R&D Systems Cat #255-SC), 100 ng/ml FMS-like trysine kinase 3 ligand (FLT3, R&D Systems Cat #308-FK), 50 ng/ml thrombopoietin (TPO, R&D Systems Cat #288-TP), and 10 µg/ml low-density lipoproteins (StemCell Technologies Cat

02698). Cells were seeded at density of 1×103 cells/ml and fresh HSC expansion media supplemented with UM171 (StemCell Technologies Cat #72914) (38 nM), SR1 (Alichem Cat #41864) (750 nM) or vehicle (0.1% DMSO) was added to keep the cell density around 3-6×10$^5$ cells/mi. For transplantation experiments, the fed-batch culture system was used as previously described (Csaszar et al., 2012, Cell Stem Cell, 10: 218-229). 1×10$^5$ CD34$^+$ or CD34$^+$CD45RA$^-$ CB cells/ml were injected into 25 ml bags (American Fluoroseal Corporation Cat #2 PF-0025) connected to a syringe loaded pumping system and maintained on an orbital shaker at 37° C. and 5% $CO_2$ in air. The pump was set to continuously deliver HSC expansion media supplemented with vehicle (0.1% DMSO), UM171 (38 nM), or combination of UM171 (38 nM) and SR1 (750 nM) at a flow rate of 0.7 µl/min.

Human CB-derived CD34$^+$ cells were expanded for 3 days with UM171 (38 nM) before they were stained with mouse anti-human EPCR antibody (APC-BioLegend Cat #351906). Total (unpurified), EPCR$^{-/low}$ and EPCR$^{Hi}$ cells were sorted and place in culture for addition 7 days in UM171 (38 nM). HSC phenotype staining and transplantation assays were then performed.

Example II

Colony-Forming Assay

Frequencies of colony-forming cells were estimated by plating 250-1000 EPCR$^-$, EPCR$^{low}$ or EPCR$^+$ cells sorted form uncultured or 7 or 12 days UM171-expanded CD34$^+$CD45RA$^-$ populations. Cells were cultured in 2% methylcellulose Iscove's Modified Dulbecco's Medium (IMDM, GIBCO Cat #12440053)-based media supplemented with 20% heat inactivated fetal bovine serum (FBS, WISENT Cat #115681), 1% bovine serum albumin (BSA, WISENT Cat #800-195-LG), 2 mM L-glutamine, 100 ng/ml SCF, 10 ng/ml IL3, 10 ng/ml IL6, 3 U/ml erythropoietin, 200 µg/ml holo-transferrin (Cat #T4132 Sigma), 10 ng/ml GM-CSF (Shenandoah Biotechnology, nc Cat #100-08), 50 ng/ml Tpo (Shenandoah Biotechnology, Inc Cat #100-05) and 10$^{-4}$ M 2-mercaptoethanol. After 14 days of culture, plates were scored for CFU-GEMMs.

Example III

Transplantation Assays

All experiments with animals were conducted under protocols approved by the University of Montreal Animal Care Committee. EPCR cell subsets purified from uncultured or expanded CD34$^+$CD45RA$^-$ CB cells were transplanted by tail vein injection into sub-lethally irradiated (250 cGy, <24 hr before transplantation) 8 to 16-week-old female NSG (NOD-Scid IL2Rγnull, Jackson Laboratory) mice. The animal technicians performed blindly the transplantation experiments.

Human cells in NSG bone marrow (BM) was monitored by flow cytometry 12 and 24 weeks post-transplantation. BM cells were collected by femoral aspiration (at week 12) or by flushing the two femurs, tibias and hips when animals were sacrificed at week 24. Criteria used for successful engraftment and evaluation of HSC activity were the same as previously reported (Fares et al., Science, 2014, 345: 1509-1512). An engraftment criterion of >0.1% human CD45$^+$ cells was used in the BM assessed by flow cytometry to establish a biologically significant cut-off. For limiting dilution analysis (LDA), cells were transplanted at 3-5 different cell doses with 5-8 mice per condition. Results from these experiments were analyzed using the ELDA software from the Walter and Eliza Hall Institute of Medical Research. Differences in HSC frequencies were analyzed using the chi-square test. *p values <0.05 were considered significant (Mann Whitney test).

For secondary transplantations, 80% of total BM cells from primary NSG recipients (24 weeks post-transplantation) were injected into secondary sub-lethally irradiated NSG mice. BM cells of the secondary mice were harvested and analyzed 18 weeks post-transplantation. Flow cytometry analysis was performed on freshly collected BM cells. Cells were treated with 1× red blood cell lysis buffer (StemCell Technologies Cat #20110), washed and stained with pacific blue-labelled anti-human CD45 (BioLegend Cat #304029), APC-eFluor 780-labelled anti-mouse CD45 (eBioscience Cat #47-0453-82), PE-labelled anti-human CD33 (BD Biosciences Cat #555450), PE-Cy7 labelled anti-human CD19 (BD Biosciences Cat #557835), FITC-labelled anti-human CD3 (BD Biosciences Cat #555332). Cells then were washed and analyzed using a FACSCanto II (BD Biosciences). BD FACSDiva software was used to analyze the flow cytometry data.

Mice that show only human lymphoid engraftment (n=3) were not taken into consideration in LDA assessment because human lymphoid cells are long-lived cells and not necessary HSC-derived.

Example IV

RNA Sequencing and Data Analysis 3-5×10$^5$ cells were sorted from CB derived CD34$^+$ HSPCs cultured for 7 days according to EPCR expression levels and preserved at −80° C. in TRIzol Reagent (Thermo Fisher Scientific Cat #15596026). cDNA libraries were constructed according to TruSeq Protocols (Illumina) and sequencing was performed using an Illumina HiSeq 2000 instrument. Casava pipeline (Illumina) and Refseq release 63 were used for subsequent mapping and quantification of gene expression. RPKM values were loaded into R and differential expression was tested using Wilcoxon rank sum statistics. Expressed genes were selected differentially based on significance (p≤0.01, Mann-Whitney test), their mean expression values in at least one of the comparison groups (≥1 RPKM) and a minimum twofold expression difference. All gene names were converted using the HGNChelper package in R to facilitate comparisons with external datasets. GSEA analyses were done using the GSEA desktop application (Broad Institute). Analyses were performed using the GSEA hallmark gene set collection and two curated HSC gene sets using standard settings. Overlap between genes associated with EPCR expression and published HSC signatures was determined using the intersect command in R. Heat maps were generated using the GENE-E software (Broad Institute). Gene expression Omnibus (GSO) Accession number GSE77128.

Example V

Construction of shEPCR Lentiviral Vectors

The MNDU-GFP-miRE vector was constructed by PCR amplification of a GFP-miR30 (shRenilla) cassette with EcoRI overhangs, and cloning into pCCL-c-MNDU3-eGFP (kindly provided by Donald Kohn[23]), replacing the GFP cassette of the parental vector. GFP-miR is thus expressed from the MNDU promoter. The shRenilla-miR30 was converted to miRE by PCR as described by Fellman et al. (2013, Cell reports, 5: 1704-1713). A stuffer sequence was added between the XhoI and EcoRI sites (replacing the shRNA) to facilitate cloning of subsequent shRNAs.

Cloning of shRNAs for EPCR into the MNDU-GFP-miRE vector was performed as described by Fellmann et al., with minor modifications. Briefly, 97mer miR template oligos were amplified with common primers which add the XhoI and EcoRI restriction sites, using Phusion polymerase (Thermo Fisher Scientific Cat # F-530) supplemented with GC buffer and DMSO for 18 cycles. PCR products as well as MNDU-miRE-GFP vector were digested with FastDigest XhoI and EcoRI (Thermo Fisher Scientific Cat #FD0694 and FD0274, respectively), gel purified using the QIAQuick Gel extraction kit (Qiagen Cat #28704), then ligated together using T4 DNA ligase (Thermo Fisher Scientific Cat # EL0011) without addition of PEG 8000 to the ligase buffer, and transformed into Stbl4 bacteria by heat shock. Colonies were screened for multiple insertions by digestion with HpaI+EcoRI (Thermo Fisher Scientific, Cat # ER1031 and FD0274, respectively), then sequence verified. Oligonucleotide sequences for PCR amplification:

```
miRE-Xho-fw-long:
                                    (SEQ ID NO: 1)
TGTGTGTGTGTGAACTCGAGAAGGTATATTGCTGTTGACAGTGAGCG.

miRE-EcoRI-rev-long:
                                    (SEQ ID NO: 2)
TCTCTCTCTCTCTCGAATTCTAGCCCCTTGAAGTCCGAGGCAGTAGGC.
```

Templates from Fellman et al:

```
PROCR.1364 (shEPCR#1):
                                    (SEQ ID NO: 3)
TGCTGTTGACAGTGAGCGATGGTGGAAATGTAAAATCCAATAGTGAAGCC

ACAGATGTATTGGATTTTACATTTC.

PROCR.1240 (shEPCR#2):
                                    (SEQ ID NO: 4)
TGCTGTTGACAGTGAGCGCTCAAAAGACAAATAATAGTGAAGCCACAGAT

GTATTATTTGGTTATAATGAATGCCTACTGCCTCGGA
```

Example VI hEPCR Lentiviral Production

HEK 293 cells were transfected with lenti-viral plasmid: 15 µg MNDU-GFP-miRE, packaging plasmids: 9 µg pLP1 and 4 µg pLP2 and envelope plasmid: 3 µg VSV-G using Lipofectamine 2000 (Thermo Fisher Scientific Cat #12566-014). Viral supernatant was collected after 48 hours and concentrated using PEG precipitation method (SBI, System Biosciences Cat # LV810A-1). Viral titers were determined to be ~1×10$^9$ TU/ml using HEK293 cells.

To validate EPCR knockdown, OCI-AML5 cells (DSMZ Cat #ACC 247) were used. As for any cell line imported in our laboratory, they were treated upon arrival for possible *mycoplasma* contamination. For viral transduction, the cells were pre-treated with protamine sulfate (10 ug/ml) for 30 min at 37° C. in 5% CO2 before the viral supernatant was added for 16 hours at a MOI of 3. The transduced cells were then washed and cultured in the presence of vehicle (DMSO) or UM171 (250 nM) for 2 additional days. Transduction (assessed via GFP) and surface EPCR knockdown efficiency were measured by flow cytometry.

CD34$^+$ cells were pre-stimulated for 24 hours in HSC expansion media. Cells were then transduced for 16 hours on retronectin (TaKaRa Cat #T100A) coated plates (20 µg/cm2) at an MOI of 100 in HSC expansion media supplemented with polybrene (3 µg/ml). Transduced CD34$^+$ cells were washed and cultured in HSC expansion media in the presence of vehicle (DMSO) or UM171 (38 nM). Transduction efficiency (assessed via GFP expression) and the expression of HSC cell surface markers were analyzed after 3 or 7 days post transduction.

Example VII shRNA Transplantation Assay

The progeny of 5×10$^3$ CD34+ cells (d0 equivalent) cultured for 6 or 7 days post-transduction were transplanted by tail vein injection into sub-lethally irradiated (250 cGy, <24 hr before transplantation) 8 to 16 week-old female NSG (NOD-Scid IL2Rγnull, Jackson Laboratory) mice. Bone marrow analysis was performed after 24 week post-transplantation to determine the human engraftment levels.

Example VIII

EPCR+ Cell Selection

The selection is carried out aseptically in a functionally-closed filtering system, such as for example but not limited to, the CliniMACS instrument. The cryopreserved CBU is placed in a sterile secondary container and thawed in a water bath. The unit is then transferred to a grade A Biosafety cabinet (BSC) for all subsequent manipulations. The CBU is transferred to a conical tube and diluted with Dextran and HSA. The diluted cell product is centrifuged and then resuspended in CliniMACS buffer that has been supplemented with Human Serum Albumin (HSA), sodium citrate, magnesium chloride and DNAse. After re-suspension, the cells are incubated with a CliniMACS EPCR$^+$ reagent and human Intravenous Immune Globulin. The stained cells are washed once with supplemented Clinimacs buffer.

The cell pellet is re-suspended in the supplemented CliniMACS buffer, and additional DNAse and IVIG are added to the suspension. The cell suspension is then transferred by syringe through a filter into a loading bag. The bag is then connected to the CliniMACS LS tubing set, and an additional bag is connected to the tubing set for the collection of the EPCR$^+$ cells. The closed-system CliniMACS LS tubing set with all associated bags connected is then moved outside of the BSC and loaded onto the CliniMACS instrument. The manufacturer's prompts on the instrument are used to connect the tubing set and perform integrity testing. The EPCR$^+$ Selection Protocol is run, following the manufacturer's directions.

At the completion of the CliniMACS instrument selection program, the bags containing the EPCR$^+$ enriched cell fraction and the EPCR$^-$ cell fraction are heat sealed and transferred to a BSC.

While the description has been described in connection with specific embodiments thereof, it will be understood that it is capable of further modifications and this application is intended to cover any variations, uses, or adaptations, including such departures from the present disclosure as come within known or customary practice within the art as may be applied to the essential features hereinbefore set forth, and as follows in the scope of the appended claims.

What is claimed is:

1. A method of expanding ex vivo human hematopoietic stem and/or progenitor cells, the method comprising:
   a) stimulating a starting population of human stem and/or progenitor cells with a cell expanding factor selected from UM171 or analogues thereof, UM171 and UM729, or UM171 and lenalidomide, wherein the expression of Endothelial Protein C Receptor (EPCR) is increased in said stimulated starting population of stem and/or progenitor cells;
   b) selecting a population of EPCR$^+$ cells from the stimulated starting population of stem and/or progenitor cells; and
   c) culturing the selected EPCR$^+$ cells thereby expanding said EPCR$^+$ cells.

2. The method of claim 1, wherein the hematopoietic stem and progenitor cells are from umbilical cord blood cells, mobilized peripheral blood cells, or bone marrow cells.

3. The method of claim 1, wherein the hematopoietic stem and progenitor cells are mobilized peripheral blood cells.

4. The method of claim 1, wherein the hematopoietic stem and progenitor cells are from human cord blood cells.

5. The method of claim 1, wherein said EPCR$^+$ cells are further enriched prior or after the selecting of the EPCR$^+$ cells by harvesting CD34$^+$, CD38$^+$, CD90$^+$, CD45RA$^+$, CD133 and/or CD49f$^+$ cells.

6. The method of claim 5, wherein said selected EPCR+ cells are CD34$^+$CD45RA$^-$ cells.

7. The method of claim 1, wherein said hematopoietic stem cells are short and long term hematopoietic stem cells.

8. The method of claim 1, further comprising stimulating the starting population with at least one cell expanding factor in combination with an aryl hydrocarbon receptor antagonist.

9. The method of claim 8, wherein the aryl hydrocarbon receptor antagonist is Stem Regenin 1 (SR1).

10. The method of claim 1, wherein said EPCR$^+$ cells are expanded in a bioreactor.

11. The method of claim 1, wherein the stem and progenitor cells are expanded in combination with at least one cytokine.

12. The method of claim 11, wherein the at least one cytokine is selected from the group consisting of IL-1, IL-3, IL-6, IL-11, G-CSF, GM-CSF, SCF, FLT3 thrombopoietin (TPO), erythropoietin, analogs thereof, and a combination.

13. The method of claim 12, wherein the at least one cytokine is SCF, FLT-3, IL6, TPO, or a combination thereof.

* * * * *